United States Patent
Levinson et al.

(10) Patent No.: US 11,177,029 B2
(45) Date of Patent: Nov. 16, 2021

(54) SYSTEMS AND TECHNIQUES FOR MONITORING SUBJECTS

(71) Applicant: Seventh Sense Biosystems, Inc., Medford, MA (US)

(72) Inventors: Douglas A. Levinson, Sherborn, MA (US); Howard Bernstein, Cambridge, MA (US)

(73) Assignee: YourBio Health, Inc., Medford, MA (US)

( * ) Notice: Subject to any disclaimer, the term of this patent is extended or adjusted under 35 U.S.C. 154(b) by 884 days.

(21) Appl. No.: 15/290,217

(22) Filed: Oct. 11, 2016

(65) Prior Publication Data

US 2017/0215790 A1    Aug. 3, 2017

Related U.S. Application Data

(63) Continuation of application No. 13/208,808, filed on Aug. 12, 2011, now abandoned.
(Continued)

(51) Int. Cl.
*G16H 20/10* (2018.01)
*G16H 20/17* (2018.01)
(Continued)

(52) U.S. Cl.
CPC ............ *G16H 20/10* (2018.01); *A61B 5/1112* (2013.01); *A61B 5/145* (2013.01);
(Continued)

(58) Field of Classification Search
None
See application file for complete search history.

(56) References Cited

U.S. PATENT DOCUMENTS

| 2,735,671 A | 2/1956 | Kuhn |
| 2,961,233 A | 11/1960 | Ullrich |

(Continued)

FOREIGN PATENT DOCUMENTS

| CN | 2065878 U | 11/1990 |
| CN | 1222334 A | 7/1999 |

(Continued)

OTHER PUBLICATIONS

International Search Report and Written Opinion for PCT/US2011/047581 dated Mar. 28, 2012.
(Continued)

*Primary Examiner* — Matthew Kremer
*Assistant Examiner* — Samuel C Kim
(74) *Attorney, Agent, or Firm* — Wolf, Greenfield & Sacks, P.C.

(57) ABSTRACT

The present invention generally relates to systems and methods for monitoring and/or providing feedback for drugs or other pharmaceuticals taken by a subject. In one aspect, the present invention is directed to devices and methods for determining a species within the skin of a subject; and producing feedback to a subject based on the determination of the species. The feedback may be, for example, visual, audible, tactile, a change in temperature, etc. In some cases, information regarding the determination of the species may be transmitted to another entity, e.g., a health care provider, a computer, a relative, etc., which may then provide feedback to the subject in some fashion. In some cases, the feedback may be directly indicative of the species. However, the feedback may also be indirect in some embodiments.

6 Claims, 7 Drawing Sheets

Related U.S. Application Data

(60) Provisional application No. 61/373,757, filed on Aug. 13, 2010.

(51) Int. Cl.

| | | |
|---|---|---|
| *A61B 10/00* | (2006.01) | |
| *G06Q 20/10* | (2012.01) | |
| *G06Q 30/02* | (2012.01) | |
| *A61B 5/15* | (2006.01) | |
| *A61B 5/154* | (2006.01) | |
| *A61B 5/145* | (2006.01) | |
| *A61B 5/157* | (2006.01) | |
| *A61B 5/151* | (2006.01) | |
| *G16H 40/63* | (2018.01) | |
| *A61B 5/00* | (2006.01) | |
| *A61B 5/11* | (2006.01) | |
| *A61M 37/00* | (2006.01) | |
| *A61M 5/172* | (2006.01) | |

(52) U.S. Cl.
CPC ...... *A61B 5/14503* (2013.01); *A61B 5/14514* (2013.01); *A61B 5/14546* (2013.01); *A61B 5/154* (2013.01); *A61B 5/157* (2013.01); *A61B 5/150022* (2013.01); *A61B 5/150099* (2013.01); *A61B 5/15113* (2013.01); *A61B 5/15125* (2013.01); *A61B 5/15142* (2013.01); *A61B 5/150175* (2013.01); *A61B 5/150389* (2013.01); *A61B 5/150412* (2013.01); *A61B 5/150503* (2013.01); *A61B 5/150755* (2013.01); *A61B 5/150809* (2013.01); *A61B 5/150824* (2013.01); *A61B 5/150854* (2013.01); *A61B 5/150862* (2013.01); *A61B 5/150969* (2013.01); *A61B 5/150984* (2013.01); *A61B 5/4833* (2013.01); *A61B 5/4839* (2013.01); *A61B 5/4848* (2013.01); *A61B 10/0045* (2013.01); *G06Q 20/10* (2013.01); *G06Q 30/02* (2013.01); *G06Q 30/0207* (2013.01); *G16H 20/17* (2018.01); *G16H 40/63* (2018.01); *A61B 5/6824* (2013.01); *A61B 2010/008* (2013.01); *A61B 2010/0009* (2013.01); *A61M 5/1723* (2013.01); *A61M 37/0015* (2013.01); *A61M 2037/0023* (2013.01); *Y02A 90/10* (2018.01)

(56) References Cited

U.S. PATENT DOCUMENTS

| | | |
|---|---|---|
| 2,976,735 A | 3/1961 | Witte |
| 3,060,429 A | 10/1962 | Winston |
| 3,072,122 A | 1/1963 | Rosenthall |
| 3,339,546 A | 9/1967 | Chen |
| 3,519,171 A | 7/1970 | Kinnavy |
| 3,551,554 A | 12/1970 | Herschler |
| 3,601,861 A | 8/1971 | Moriwaki |
| 3,645,253 A | 2/1972 | Goverde et al. |
| 3,711,602 A | 1/1973 | Herschler |
| 3,711,606 A | 1/1973 | Herschler |
| 3,740,421 A | 6/1973 | Schmolka |
| 3,753,432 A | 8/1973 | Guerra |
| 3,761,013 A | 9/1973 | Schuster |
| 3,908,657 A | 9/1975 | Kowarski |
| 3,964,482 A | 6/1976 | Gerstel et al. |
| 4,103,684 A | 8/1978 | Ismach |
| 4,150,744 A | 4/1979 | Fennimore |
| 4,203,520 A | 5/1980 | Schuster |
| 4,253,460 A | 3/1981 | Chen et al. |
| 4,280,509 A | 7/1981 | Bethkenhagen et al. |
| 4,329,999 A | 5/1982 | Phillips |
| 4,340,067 A | 7/1982 | Rattenborg |
| 4,437,567 A | 3/1984 | Jeng |
| 4,537,776 A | 8/1985 | Cooper |
| 4,553,552 A | 11/1985 | Valdespino et al. |
| 4,557,943 A | 12/1985 | Rosler et al. |
| 4,572,210 A | 2/1986 | McKinnon |
| 4,615,697 A | 10/1986 | Robinson |
| 4,621,268 A | 11/1986 | Keeling et al. |
| 4,637,403 A | 1/1987 | Garcia et al. |
| 4,696,309 A | 9/1987 | Stephan |
| 4,706,676 A | 11/1987 | Peck |
| 4,740,365 A | 4/1988 | Yukimatsu et al. |
| 4,756,314 A | 7/1988 | Eckenhoff et al. |
| 4,764,378 A | 8/1988 | Keith et al. |
| 4,772,470 A | 9/1988 | Inoue et al. |
| 4,796,644 A | 1/1989 | Polaschegg |
| 4,820,720 A | 4/1989 | Sanders et al. |
| 4,821,733 A | 4/1989 | Peck |
| 4,855,298 A | 8/1989 | Yamada et al. |
| 4,855,989 A | 8/1989 | Gyger |
| 4,856,533 A | 8/1989 | Anraku et al. |
| 4,863,970 A | 9/1989 | Patel et al. |
| 4,883,068 A | 11/1989 | Dechow |
| 4,908,404 A | 3/1990 | Benedict et al. |
| 4,957,108 A | 9/1990 | Schoendorfer et al. |
| 4,971,068 A | 11/1990 | Sahi |
| 4,973,468 A | 11/1990 | Chiang et al. |
| 5,006,342 A | 4/1991 | Cleary et al. |
| 5,014,718 A | 5/1991 | Mitchen |
| 5,015,677 A | 5/1991 | Benedict et al. |
| 5,036,861 A | 8/1991 | Sembrowich et al. |
| 5,054,499 A | 10/1991 | Swierczek |
| 5,076,273 A | 12/1991 | Schoendorfer et al. |
| 5,108,927 A | 4/1992 | Dorn |
| 5,145,565 A | 9/1992 | Kater et al. |
| 5,161,532 A | 11/1992 | Joseph |
| 5,174,291 A | 12/1992 | Schoonen et al. |
| 5,201,324 A | 4/1993 | Swierczek |
| 5,213,568 A | 5/1993 | Lattin et al. |
| 5,231,993 A | 8/1993 | Haber et al. |
| 5,238,655 A | 8/1993 | Laible et al. |
| 5,279,294 A | 1/1994 | Anderson et al. |
| 5,320,607 A | 6/1994 | Ishibashi |
| 5,342,397 A | 8/1994 | Guido |
| 5,379,895 A | 1/1995 | Foslien |
| 5,402,798 A | 4/1995 | Swierczek et al. |
| 5,438,984 A | 8/1995 | Schoendorfer |
| 5,441,048 A | 8/1995 | Schoendorfer |
| 5,441,490 A | 8/1995 | Svedman |
| 5,443,080 A | 8/1995 | D'Angelo et al. |
| 5,445,611 A | 8/1995 | Eppstein et al. |
| 5,458,140 A | 10/1995 | Eppstein et al. |
| 5,504,011 A | 4/1996 | Gavin et al. |
| 5,505,212 A | 4/1996 | Keljmann et al. |
| 5,507,288 A | 4/1996 | Bocker et al. |
| 5,516,487 A | 5/1996 | Rosenthal et al. |
| 5,520,727 A | 5/1996 | Vreeland et al. |
| 5,529,581 A | 6/1996 | Cusack |
| 5,540,709 A | 7/1996 | Ramel |
| 5,552,118 A | 9/1996 | Mayer |
| 5,560,543 A | 10/1996 | Smith et al. |
| 5,574,134 A | 11/1996 | Waite |
| 5,580,794 A | 12/1996 | Allen |
| 5,582,184 A | 12/1996 | Erickson et al. |
| 5,591,403 A | 1/1997 | Gavin et al. |
| 5,636,640 A | 6/1997 | Staehlin |
| 5,638,815 A | 6/1997 | Schoendorfer |
| 5,662,127 A | 9/1997 | De Vaughn |
| 5,676,144 A | 10/1997 | Schoendorfer |
| 5,680,872 A | 10/1997 | Sesekura et al. |
| 5,682,233 A | 10/1997 | Brinda |
| 5,685,875 A | 11/1997 | Hlavinka et al. |
| 5,701,910 A | 12/1997 | Powles et al. |
| 5,714,390 A | 2/1998 | Hallowitz et al. |
| 5,741,138 A | 4/1998 | Rice et al. |
| 5,746,217 A | 5/1998 | Erickson et al. |
| 5,800,420 A | 9/1998 | Gross et al. |
| 5,800,781 A | 9/1998 | Gavin et al. |
| 5,807,375 A | 9/1998 | Gross et al. |
| 5,811,108 A | 9/1998 | Goeringer |

(56) References Cited

U.S. PATENT DOCUMENTS

| | | |
|---|---|---|
| 5,813,614 A | 9/1998 | Coffee |
| 5,817,011 A | 10/1998 | Schoendorfer |
| 5,817,012 A | 10/1998 | Schoendorfer |
| 5,820,570 A | 10/1998 | Erickson et al. |
| 5,820,622 A | 10/1998 | Gross et al. |
| 5,823,973 A | 10/1998 | Racchini et al. |
| 5,857,983 A | 1/1999 | Douglas et al. |
| 5,858,188 A | 1/1999 | Soane et al. |
| 5,873,900 A | 2/1999 | Maurer et al. |
| 5,876,675 A | 3/1999 | Kennedy |
| 5,879,310 A | 3/1999 | Sopp et al. |
| 5,879,311 A | 3/1999 | Duchon et al. |
| 5,879,367 A | 3/1999 | Latterell et al. |
| 5,885,211 A | 3/1999 | Eppstein et al. |
| 5,891,053 A | 4/1999 | Sesekura |
| 5,897,508 A | 4/1999 | Konrad |
| 5,944,662 A | 8/1999 | Schoendorfer |
| 5,951,492 A | 9/1999 | Douglas et al. |
| 5,951,493 A | 9/1999 | Douglas et al. |
| 5,955,096 A | 9/1999 | Santos et al. |
| 5,963,136 A | 10/1999 | O'Brien |
| 5,964,718 A | 10/1999 | Duchon et al. |
| 5,972,386 A | 10/1999 | Burgoyne |
| 5,985,312 A | 11/1999 | Jacob et al. |
| 5,998,588 A | 12/1999 | Hoffman et al. |
| 6,007,845 A | 12/1999 | Domb et al. |
| 6,015,392 A | 1/2000 | Douglas et al. |
| 6,024,710 A | 2/2000 | Miller et al. |
| 6,027,459 A | 2/2000 | Shain et al. |
| 6,040,135 A | 3/2000 | Tyrell |
| 6,044,303 A | 3/2000 | Agarwala et al. |
| 6,048,337 A | 4/2000 | Svedman |
| 6,050,988 A | 4/2000 | Zuck |
| 6,063,029 A | 5/2000 | Saita et al. |
| 6,063,039 A | 5/2000 | Cunningham et al. |
| 6,063,365 A | 5/2000 | Shefer et al. |
| 6,066,103 A | 5/2000 | Duchon et al. |
| 6,071,249 A | 6/2000 | Cunningham et al. |
| 6,071,250 A | 6/2000 | Douglas et al. |
| 6,071,251 A | 6/2000 | Cunningham et al. |
| 6,080,116 A | 6/2000 | Erickson et al. |
| 6,083,196 A | 7/2000 | Trautman et al. |
| 6,091,975 A | 7/2000 | Daddona et al. |
| 6,093,156 A | 7/2000 | Cunningham et al. |
| 6,099,484 A | 8/2000 | Douglas et al. |
| 6,107,102 A | 8/2000 | Ferrari |
| 6,126,899 A | 10/2000 | Woudenberg et al. |
| 6,132,449 A | 10/2000 | Lum et al. |
| 6,132,702 A | 10/2000 | Witt et al. |
| 6,133,318 A | 10/2000 | Hart |
| 6,152,889 A | 11/2000 | Sopp et al. |
| 6,152,942 A | 11/2000 | Brenneman et al. |
| 6,155,992 A | 12/2000 | Henning et al. |
| 6,162,639 A | 12/2000 | Douglas |
| 6,190,315 B1 | 2/2001 | Kost et al. |
| 6,192,890 B1 | 2/2001 | Levy et al. |
| 6,203,504 B1 | 3/2001 | Latterell et al. |
| 6,206,841 B1 | 3/2001 | Cunningham et al. |
| 6,219,574 B1 | 4/2001 | Cormier et al. |
| 6,228,100 B1 | 5/2001 | Schraga |
| 6,230,051 B1 | 5/2001 | Cormier et al. |
| 6,234,990 B1 | 5/2001 | Rowe et al. |
| 6,235,313 B1 | 5/2001 | Mathiowitz et al. |
| 6,252,129 B1 | 6/2001 | Coffee |
| 6,267,724 B1 | 7/2001 | Taylor |
| 6,283,926 B1 | 9/2001 | Cunningham et al. |
| 6,306,104 B1 | 10/2001 | Cunningham et al. |
| 6,306,993 B1 | 10/2001 | Rothbard et al. |
| 6,309,887 B1 | 10/2001 | Ray |
| 6,315,951 B1 | 11/2001 | Markart |
| 6,319,210 B1 | 11/2001 | Douglas et al. |
| 6,322,574 B1 | 11/2001 | Llyod |
| 6,332,871 B1 | 12/2001 | Douglas et al. |
| 6,334,856 B1 | 1/2002 | Allen et al. |
| 6,340,354 B1 | 1/2002 | Rambin |
| 6,349,229 B1 | 2/2002 | Watanabe et al. |
| 6,349,850 B1 | 2/2002 | Cheikh |
| 6,361,944 B1 | 3/2002 | Mirkin et al. |
| 6,364,890 B1 | 4/2002 | Lum et al. |
| 6,379,317 B1 | 4/2002 | Kintzig et al. |
| 6,379,324 B1 | 4/2002 | Gartstein et al. |
| 6,391,471 B1 | 5/2002 | Hiraoka et al. |
| 6,394,952 B1 | 5/2002 | Anderson et al. |
| 6,406,919 B1 | 6/2002 | Tyrrell |
| 6,409,679 B2 | 6/2002 | Pyo |
| 6,436,078 B1 | 8/2002 | Svedman |
| 6,440,096 B1 | 8/2002 | Lastovich et al. |
| 6,455,324 B1 | 9/2002 | Douglas |
| 6,461,644 B1 | 10/2002 | Jackson et al. |
| 6,464,649 B1 | 10/2002 | Duchon et al. |
| 6,465,002 B1 | 10/2002 | Mathiowitz et al. |
| 6,485,439 B1 | 11/2002 | Roe et al. |
| 6,485,703 B1 | 11/2002 | Cote et al. |
| 6,491,657 B2 | 12/2002 | Rowe et al. |
| 6,491,902 B2 | 12/2002 | Shefer et al. |
| 6,501,976 B1 | 12/2002 | Sohrab |
| 6,502,697 B1 | 1/2003 | Crampton et al. |
| 6,503,209 B2 | 1/2003 | Hakky et al. |
| 6,503,231 B1 | 1/2003 | Prausnitz et al. |
| 6,506,168 B1 | 1/2003 | Fathallah et al. |
| 6,527,716 B1 | 3/2003 | Eppstein |
| 6,532,386 B2 | 3/2003 | Sun et al. |
| 6,537,243 B1 | 3/2003 | Henning et al. |
| 6,537,264 B1 | 3/2003 | Cormier et al. |
| 6,538,089 B1 | 3/2003 | Samra et al. |
| 6,540,675 B2 | 4/2003 | Aceti et al. |
| 6,548,264 B1 | 4/2003 | Tan et al. |
| 6,558,361 B1 | 5/2003 | Yeshurun |
| 6,562,014 B2 | 5/2003 | Lin et al. |
| 6,589,562 B1 | 7/2003 | Shefer et al. |
| 6,591,124 B2 | 7/2003 | Sherman et al. |
| 6,602,205 B1 | 8/2003 | Erickson et al. |
| 6,603,987 B2 | 8/2003 | Whitson |
| 6,607,495 B1 | 8/2003 | Skalak et al. |
| 6,607,513 B1 | 8/2003 | Down et al. |
| 6,611,707 B1 | 8/2003 | Prausnitz et al. |
| 6,614,522 B1 | 9/2003 | Sopp et al. |
| 6,620,123 B1 | 9/2003 | Mitragotri et al. |
| 6,624,882 B2 | 9/2003 | Sopp et al. |
| 6,626,884 B1 | 9/2003 | Dillon et al. |
| 6,629,057 B2 | 9/2003 | Zweig et al. |
| 6,652,478 B1 | 11/2003 | Gartstein et al. |
| 6,656,147 B1 | 12/2003 | Gertsek et al. |
| 6,660,527 B2 | 12/2003 | Stroup |
| 6,669,961 B2 | 12/2003 | Kim et al. |
| 6,678,554 B1 | 1/2004 | Sun et al. |
| 6,685,921 B2 | 2/2004 | Lawlor |
| 6,689,100 B2 | 2/2004 | Connelly et al. |
| 6,696,075 B2 | 2/2004 | Mathiowitz et al. |
| 6,706,000 B2 | 3/2004 | Perez et al. |
| 6,706,159 B2 | 3/2004 | Moerman et al. |
| 6,712,776 B2 | 3/2004 | Latterell et al. |
| 6,712,792 B2 | 3/2004 | Leong |
| 6,741,877 B1 | 5/2004 | Shults et al. |
| 6,743,211 B1 | 6/2004 | Prausnitz et al. |
| 6,749,575 B2 | 6/2004 | Matriano et al. |
| 6,765,081 B2 | 7/2004 | Lin et al. |
| 6,766,817 B2 | 7/2004 | da Silva |
| 6,768,920 B2 | 7/2004 | Lange et al. |
| 6,783,502 B2 | 8/2004 | Orloff et al. |
| 6,786,874 B2 | 9/2004 | Grace et al. |
| 6,793,633 B2 | 9/2004 | Douglas et al. |
| 6,798,920 B1 | 9/2004 | Wells et al. |
| 6,800,122 B2 | 10/2004 | Anderson et al. |
| 6,811,090 B2 | 11/2004 | Yogi et al. |
| 6,814,760 B2 | 11/2004 | Anderson et al. |
| 6,825,161 B2 | 11/2004 | Shefer et al. |
| 6,826,426 B2 | 11/2004 | Lange et al. |
| 6,837,858 B2 | 1/2005 | Cunningham et al. |
| 6,855,133 B2 | 2/2005 | Svedman |
| 6,860,873 B2 | 3/2005 | Allen et al. |
| 6,878,120 B2 | 4/2005 | Roe et al. |
| 6,896,666 B2 | 5/2005 | Kochamba |
| 6,899,851 B2 | 5/2005 | Allen et al. |

(56) References Cited

U.S. PATENT DOCUMENTS

| | | |
|---|---|---|
| 6,908,448 B2 | 6/2005 | Redding, Jr. |
| 6,918,404 B2 | 7/2005 | Dias da Silva |
| 6,918,901 B1 | 7/2005 | Theeuwes et al. |
| 6,923,764 B2 | 8/2005 | Aceti et al. |
| 6,925,317 B1 | 8/2005 | Samuels et al. |
| 6,931,277 B1 | 8/2005 | Yuzhakov et al. |
| 6,940,591 B2 | 9/2005 | Sopp et al. |
| 6,952,604 B2 | 10/2005 | DeNuzzio et al. |
| 6,969,351 B2 | 11/2005 | Knoll |
| 6,969,359 B2 | 11/2005 | Duchon et al. |
| 6,990,367 B2 | 1/2006 | Kiser et al. |
| 6,997,886 B2 | 2/2006 | Latterell et al. |
| 7,001,343 B2 | 2/2006 | Erickson et al. |
| 7,001,344 B2 | 2/2006 | Freeman et al. |
| 7,004,928 B2 | 2/2006 | Aceti et al. |
| 7,008,384 B2 | 3/2006 | Tapper |
| 7,014,615 B2 | 3/2006 | Erickson et al. |
| 7,025,774 B2 | 4/2006 | Freeman et al. |
| 7,037,277 B1 | 5/2006 | Smith et al. |
| 7,041,067 B2 | 5/2006 | Sopp et al. |
| 7,041,068 B2 | 5/2006 | Freeman et al. |
| 7,047,070 B2 | 5/2006 | Wilkinson et al. |
| 7,066,586 B2 | 6/2006 | da Silva |
| 7,066,885 B2 | 6/2006 | Erickson et al. |
| 7,097,631 B2 | 8/2006 | Trautman et al. |
| 7,131,987 B2 | 11/2006 | Sherman et al. |
| 7,133,717 B2 | 11/2006 | Coston et al. |
| 7,137,957 B2 | 11/2006 | Erickson et al. |
| 7,150,755 B2 | 12/2006 | Levaughn et al. |
| 7,172,071 B2 | 2/2007 | Hawkins |
| 7,174,199 B2 | 2/2007 | Berner et al. |
| 7,182,910 B2 | 2/2007 | Allen et al. |
| 7,185,764 B2 | 3/2007 | Lee et al. |
| 7,235,056 B2 | 6/2007 | Duchon et al. |
| 7,247,144 B2 | 7/2007 | Douglas et al. |
| 7,264,627 B2 | 9/2007 | Perez |
| 7,316,671 B2 | 1/2008 | Lastovich et al. |
| 7,335,166 B2 | 2/2008 | Faupel et al. |
| 7,344,499 B1 | 3/2008 | Prausnitz et al. |
| 7,344,587 B2 | 3/2008 | Khan et al. |
| 7,374,545 B2 | 5/2008 | Alroy |
| 7,374,949 B2 | 5/2008 | Kuriger |
| 7,402,441 B2 | 7/2008 | Lowe et al. |
| 7,413,868 B2 | 8/2008 | Kauvar et al. |
| 7,422,567 B2 | 9/2008 | Lastovich et al. |
| 7,429,258 B2 | 9/2008 | Angel et al. |
| 7,537,590 B2 | 5/2009 | Santini et al. |
| 7,544,185 B2 | 6/2009 | Bengtsson |
| 7,556,615 B2 | 7/2009 | Pettis et al. |
| 7,572,237 B2 | 8/2009 | Saikley et al. |
| 7,575,717 B2 | 8/2009 | Cooke et al. |
| 7,585,278 B2 | 9/2009 | Aceti et al. |
| 7,585,412 B2 | 9/2009 | Gorsuch et al. |
| 7,631,760 B2 | 12/2009 | Guelzow et al. |
| 7,758,518 B2 | 7/2010 | Perez et al. |
| 7,767,017 B2 | 8/2010 | Lahann et al. |
| 7,811,236 B2 | 10/2010 | List et al. |
| 7,811,302 B2 | 10/2010 | Steg |
| 7,833,172 B2 | 11/2010 | Hein et al. |
| 7,883,473 B2 | 2/2011 | LeVaughn et al. |
| 7,896,830 B2 | 3/2011 | Gura et al. |
| 7,942,827 B2 | 5/2011 | Mir et al. |
| 7,947,772 B2 | 5/2011 | Lahann |
| 8,043,480 B2 | 10/2011 | Lahann et al. |
| 8,052,849 B2 | 11/2011 | Lahann et al. |
| 8,058,077 B2 | 11/2011 | Groll et al. |
| 8,071,384 B2 | 12/2011 | Burke et al. |
| 8,075,826 B2 | 12/2011 | Lastovich et al. |
| 8,133,191 B2 | 3/2012 | Rosenberg et al. |
| 8,187,708 B2 | 5/2012 | Lahann et al. |
| 8,202,240 B2 | 6/2012 | Felt et al. |
| 8,241,651 B2 | 8/2012 | Lahann |
| 8,246,582 B2 | 8/2012 | Angel et al. |
| 8,344,028 B2 | 1/2013 | Xu et al. |
| 8,383,044 B2 | 2/2013 | Davis et al. |
| 8,460,210 B2 | 6/2013 | Jacobs |
| 8,465,425 B2 | 6/2013 | Heller et al. |
| 8,517,938 B2 | 8/2013 | Eisenhardt et al. |
| 8,523,894 B2 | 9/2013 | Schmelzeisen-Redeker et al. |
| 8,530,231 B2 | 9/2013 | Nakae et al. |
| 8,561,795 B2 | 10/2013 | Schott |
| 8,628,724 B2 | 1/2014 | Kuenstner |
| 8,647,575 B2 | 2/2014 | Ohashi |
| 8,808,202 B2 | 8/2014 | Brancazio |
| 8,821,412 B2 | 9/2014 | Gonzalez-Zugasti et al. |
| 8,821,446 B2 | 9/2014 | Trautman et al. |
| 8,827,971 B2 | 9/2014 | Chickering, III et al. |
| 8,882,794 B2 | 10/2014 | LeVaughn et al. |
| 8,900,180 B2 | 12/2014 | Wolter et al. |
| 8,934,955 B2 | 1/2015 | Schraga |
| 8,971,980 B2 | 3/2015 | Mace et al. |
| 9,028,426 B2 | 5/2015 | List et al. |
| 9,033,898 B2 | 5/2015 | Chickering, III et al. |
| 9,033,989 B2 | 5/2015 | Wolfson et al. |
| 9,039,638 B2 | 5/2015 | Arnitz |
| 9,041,541 B2 | 5/2015 | Levinson et al. |
| 9,101,302 B2 | 8/2015 | Mace et al. |
| 9,113,836 B2 | 8/2015 | Bernstein et al. |
| 9,119,578 B2 | 9/2015 | Haghgooie et al. |
| 9,295,417 B2 | 3/2016 | Haghgooie et al. |
| 9,730,624 B2 | 8/2017 | Gonzalez-Zugasti et al. |
| 9,775,551 B2 | 10/2017 | Bernstein et al. |
| 10,188,335 B2 | 1/2019 | Haghgooie et al. |
| 10,799,166 B2 | 10/2020 | Gonzalez-Zugasti et al. |
| 10,835,163 B2 | 11/2020 | Haghgooie et al. |
| 10,939,860 B2 | 3/2021 | Levinson et al. |
| 2001/0005772 A1 | 6/2001 | Kisakibaru |
| 2002/0010414 A1 | 1/2002 | Coston et al. |
| 2002/0013538 A1 | 1/2002 | Teller |
| 2002/0065453 A1 | 5/2002 | Lesho et al. |
| 2002/0076443 A1 | 6/2002 | Stein et al. |
| 2002/0077584 A1 | 6/2002 | Lin et al. |
| 2002/0082543 A1 | 6/2002 | Park et al. |
| 2002/0087056 A1* | 7/2002 | Aceti ............ A61B 5/150511 600/309 |
| 2002/0099308 A1 | 7/2002 | Bojan et al. |
| 2002/0099356 A1 | 7/2002 | Unger et al. |
| 2002/0112981 A1 | 8/2002 | Cooper et al. |
| 2002/0115967 A1 | 8/2002 | Svedman |
| 2002/0119136 A1 | 8/2002 | Johansen |
| 2002/0130042 A1 | 9/2002 | Moerman et al. |
| 2002/0130093 A1 | 9/2002 | Ferrara et al. |
| 2002/0138049 A1 | 9/2002 | Allen |
| 2002/0143320 A1 | 10/2002 | Levin |
| 2002/0168290 A1 | 11/2002 | Yuzhakov et al. |
| 2002/0169393 A1 | 11/2002 | Cunningham et al. |
| 2002/0169394 A1 | 11/2002 | Eppstein et al. |
| 2002/0169411 A1 | 11/2002 | Sherman et al. |
| 2002/0177761 A1 | 11/2002 | Orloff et al. |
| 2002/0187556 A1 | 12/2002 | Shartle et al. |
| 2002/0188221 A1 | 12/2002 | Sohrab |
| 2003/0004437 A1 | 1/2003 | Collins et al. |
| 2003/0040682 A1 | 2/2003 | Tapper |
| 2003/0055326 A1 | 3/2003 | Sohrab |
| 2003/0083618 A1 | 5/2003 | Angel et al. |
| 2003/0083645 A1 | 5/2003 | Angel et al. |
| 2003/0083685 A1 | 5/2003 | Freeman et al. |
| 2003/0100846 A1 | 5/2003 | Custer et al. |
| 2003/0109807 A1 | 6/2003 | Knoll |
| 2003/0113540 A1 | 6/2003 | Anderson et al. |
| 2003/0135158 A1 | 7/2003 | Gonnelli |
| 2003/0135167 A1 | 7/2003 | Gonnelli |
| 2003/0135201 A1 | 7/2003 | Gonnelli |
| 2003/0135333 A1 | 7/2003 | Aceti et al. |
| 2003/0143746 A1 | 7/2003 | Sage |
| 2003/0159615 A1 | 8/2003 | Anderson et al. |
| 2003/0162304 A1 | 8/2003 | Dority et al. |
| 2003/0181863 A1 | 9/2003 | Ackley et al. |
| 2003/0187394 A1 | 10/2003 | Wilkinson et al. |
| 2003/0187395 A1 | 10/2003 | Gabel et al. |
| 2003/0195398 A1 | 10/2003 | Suzuki et al. |
| 2003/0204148 A1 | 10/2003 | Lange et al. |
| 2003/0208138 A1 | 11/2003 | Olson |
| 2003/0212344 A1 | 11/2003 | Yuzhakov et al. |

(56) References Cited

U.S. PATENT DOCUMENTS

| | | |
|---|---|---|
| 2003/0212345 A1 | 11/2003 | McAllister et al. |
| 2003/0212347 A1 | 11/2003 | Sohrab |
| 2003/0212423 A1 | 11/2003 | Pugh et al. |
| 2003/0228367 A1 | 12/2003 | Mathiowitz et al. |
| 2004/0010207 A1 | 1/2004 | Flaherty et al. |
| 2004/0053894 A1 | 3/2004 | Mazess et al. |
| 2004/0058458 A1 | 3/2004 | Anker et al. |
| 2004/0087990 A1 | 5/2004 | Boecker et al. |
| 2004/0096959 A1 | 5/2004 | Stiene et al. |
| 2004/0098009 A1 | 5/2004 | Boecker et al. |
| 2004/0102717 A1 | 5/2004 | Qi |
| 2004/0106904 A1 | 6/2004 | Gonnelli et al. |
| 2004/0133126 A1 | 7/2004 | McNenny |
| 2004/0137640 A1 | 7/2004 | Hirao et al. |
| 2004/0138688 A1 | 7/2004 | Giraud |
| 2004/0162521 A1 | 8/2004 | Bengtsson |
| 2004/0163987 A1 | 8/2004 | Allen |
| 2004/0171980 A1 | 9/2004 | Mitragotri et al. |
| 2004/0199103 A1 | 10/2004 | Kwon |
| 2004/0204744 A1 | 10/2004 | Penner et al. |
| 2004/0236250 A1 | 11/2004 | Hodges et al. |
| 2004/0247016 A1 | 12/2004 | Faries et al. |
| 2004/0249310 A1 | 12/2004 | Shartle et al. |
| 2004/0253185 A1 | 12/2004 | Herweck et al. |
| 2005/0000514 A1 | 1/2005 | Sullivan et al. |
| 2005/0015055 A1 | 1/2005 | Yang |
| 2005/0019902 A1 | 1/2005 | Mathies et al. |
| 2005/0027176 A1 | 2/2005 | Xie |
| 2005/0027308 A1 | 2/2005 | Davis et al. |
| 2005/0033197 A1 | 2/2005 | Cottler |
| 2005/0038669 A1 | 2/2005 | Sachdeva et al. |
| 2005/0054907 A1 | 3/2005 | Page et al. |
| 2005/0064529 A1 | 3/2005 | Kwon |
| 2005/0069925 A1 | 3/2005 | Ford et al. |
| 2005/0070819 A1 | 3/2005 | Poux et al. |
| 2005/0085838 A1 | 4/2005 | Thompson et al. |
| 2005/0090766 A1 | 4/2005 | Montanari |
| 2005/0106066 A1 | 5/2005 | Saltsman et al. |
| 2005/0106713 A1 | 5/2005 | Phan et al. |
| 2005/0137481 A1 | 6/2005 | Sheard et al. |
| 2005/0137531 A1 | 6/2005 | Prausnitz et al. |
| 2005/0137536 A1 | 6/2005 | Gonnelli |
| 2005/0172852 A1 | 8/2005 | Anderson et al. |
| 2005/0182307 A1 | 8/2005 | Currie et al. |
| 2005/0196747 A1 | 9/2005 | Stiene |
| 2005/0201974 A1 | 9/2005 | Schestopol et al. |
| 2005/0203360 A1 | 9/2005 | Brauker et al. |
| 2005/0215923 A1 | 9/2005 | Wiegel |
| 2005/0221276 A1 | 10/2005 | Rozakis et al. |
| 2005/0227269 A1 | 10/2005 | Lloyd, Jr. et al. |
| 2005/0228313 A1 | 10/2005 | Kaler et al. |
| 2005/0245844 A1 | 11/2005 | Mace et al. |
| 2005/0249672 A1 | 11/2005 | Bolbot |
| 2005/0251152 A1 | 11/2005 | Herweck et al. |
| 2005/0261632 A1 | 11/2005 | Xu |
| 2005/0261639 A1 | 11/2005 | Herweck |
| 2005/0267422 A1 | 12/2005 | Kriesel |
| 2006/0001551 A1 | 1/2006 | Kraft et al. |
| 2006/0004271 A1 | 1/2006 | Peyser et al. |
| 2006/0004303 A1 | 1/2006 | Weidenhaupt et al. |
| 2006/0030790 A1 | 2/2006 | Braig et al. |
| 2006/0036187 A1 | 2/2006 | Vos et al. |
| 2006/0058602 A1 | 3/2006 | Kwiatkowski et al. |
| 2006/0089566 A1 | 4/2006 | DeHart |
| 2006/0091669 A1 | 5/2006 | Wilkinson |
| 2006/0100654 A1 | 5/2006 | Fukuda et al. |
| 2006/0129065 A1 | 6/2006 | Matsumoto et al. |
| 2006/0142651 A1 | 6/2006 | Brister et al. |
| 2006/0157362 A1 | 7/2006 | Schraga |
| 2006/0182738 A1* | 8/2006 | Holmes ............ A61B 5/150282 424/130.1 |
| 2006/0189895 A1 | 8/2006 | Neel et al. |
| 2006/0200046 A1 | 9/2006 | Windus-Smith et al. |
| 2006/0202385 A1 | 9/2006 | Xu et al. |
| 2006/0228259 A1 | 10/2006 | Samsoondar |
| 2006/0257883 A1 | 11/2006 | Bjorkaker et al. |
| 2006/0258959 A1 | 11/2006 | Sode |
| 2006/0259195 A1 | 11/2006 | Eliuk et al. |
| 2006/0264779 A1 | 11/2006 | Kemp et al. |
| 2006/0264782 A1 | 11/2006 | Holmes et al. |
| 2007/0004989 A1 | 1/2007 | Dhillon |
| 2007/0016446 A1 | 1/2007 | Brown |
| 2007/0027427 A1 | 2/2007 | Trautman et al. |
| 2007/0031283 A1 | 2/2007 | Davis et al. |
| 2007/0031293 A1 | 2/2007 | Beatty |
| 2007/0036686 A1 | 2/2007 | Hatamian et al. |
| 2007/0046476 A1 | 3/2007 | Hinkamp |
| 2007/0054119 A1 | 3/2007 | Garstecki et al. |
| 2007/0066934 A1 | 3/2007 | Etheredge et al. |
| 2007/0078414 A1 | 4/2007 | McAllister et al. |
| 2007/0083131 A1 | 4/2007 | Escutia et al. |
| 2007/0088248 A1 | 4/2007 | Glenn et al. |
| 2007/0092637 A1 | 4/2007 | Brown et al. |
| 2007/0100219 A1 | 5/2007 | Sweitzer et al. |
| 2007/0105176 A1 | 5/2007 | Ibey et al. |
| 2007/0112180 A1 | 5/2007 | Gray et al. |
| 2007/0123801 A1 | 5/2007 | Goldberger et al. |
| 2007/0129618 A1 | 6/2007 | Goldberger et al. |
| 2007/0161926 A1 | 7/2007 | Imamura et al. |
| 2007/0161964 A1 | 7/2007 | Yukhazov |
| 2007/0167340 A1 | 7/2007 | Barthel et al. |
| 2007/0169411 A1 | 7/2007 | Thiessen et al. |
| 2007/0173740 A1 | 7/2007 | Chan et al. |
| 2007/0179404 A1 | 8/2007 | Escutia et al. |
| 2007/0185432 A1 | 8/2007 | Etheredge et al. |
| 2007/0185515 A1 | 8/2007 | Stout |
| 2007/0208275 A1 | 9/2007 | Vinogradov et al. |
| 2007/0213638 A1 | 9/2007 | Herbrechtsmeier et al. |
| 2007/0225676 A1 | 9/2007 | Prausnitz et al. |
| 2007/0231355 A1 | 10/2007 | Quadir et al. |
| 2007/0232956 A1 | 10/2007 | Harman et al. |
| 2007/0233199 A1 | 10/2007 | Moore et al. |
| 2007/0237800 A1 | 10/2007 | Lahann |
| 2007/0238943 A1 | 10/2007 | Poulsen et al. |
| 2007/0249962 A1 | 10/2007 | Alden et al. |
| 2007/0272738 A1 | 11/2007 | Berkun |
| 2007/0275193 A1 | 11/2007 | deSimone et al. |
| 2008/0009763 A1 | 1/2008 | Chiou et al. |
| 2008/0014627 A1 | 1/2008 | Merchant et al. |
| 2008/0033319 A1 | 2/2008 | Kloepfer et al. |
| 2008/0051689 A1 | 2/2008 | Gura et al. |
| 2008/0077096 A1 | 3/2008 | Nakamura et al. |
| 2008/0077430 A1 | 3/2008 | Singer et al. |
| 2008/0081695 A1 | 4/2008 | Patchen |
| 2008/0086051 A1 | 4/2008 | Voegele |
| 2008/0099478 A1 | 5/2008 | Gleich |
| 2008/0103434 A1 | 5/2008 | Lastovich et al. |
| 2008/0108958 A1 | 5/2008 | Carter et al. |
| 2008/0108959 A1 | 5/2008 | Jung et al. |
| 2008/0112886 A1 | 5/2008 | Mitragotri et al. |
| 2008/0125673 A1 | 5/2008 | Carano et al. |
| 2008/0125743 A1 | 5/2008 | Yuzhakov |
| 2008/0129486 A1 | 6/2008 | Jeckelmann et al. |
| 2008/0140049 A1 | 6/2008 | Kirby |
| 2008/0154107 A1 | 6/2008 | Jina |
| 2008/0167535 A1 | 7/2008 | Stivoric et al. |
| 2008/0167613 A1 | 7/2008 | Khouri et al. |
| 2008/0183140 A1 | 7/2008 | Paproski et al. |
| 2008/0183144 A1 | 7/2008 | Trautman et al. |
| 2008/0200791 A1 | 8/2008 | Simpson et al. |
| 2008/0200838 A1 | 8/2008 | Goldberger et al. |
| 2008/0217391 A1 | 9/2008 | Roof et al. |
| 2008/0220411 A1 | 9/2008 | McNaughton et al. |
| 2008/0221407 A1 | 9/2008 | Baker |
| 2008/0267537 A1 | 10/2008 | Thuries |
| 2008/0269666 A1 | 10/2008 | Wang et al. |
| 2008/0275327 A1 | 11/2008 | Faarbaek et al. |
| 2008/0275378 A1 | 11/2008 | Herndon |
| 2008/0281290 A1 | 11/2008 | Yodfat et al. |
| 2008/0283603 A1 | 11/2008 | Barron et al. |
| 2008/0300508 A1 | 12/2008 | Tomer |
| 2008/0315994 A1 | 12/2008 | Maltseff et al. |
| 2008/0319347 A1 | 12/2008 | Keren |
| 2009/0036795 A1 | 2/2009 | Duineveld et al. |

(56) References Cited

U.S. PATENT DOCUMENTS

| | | |
|---|---|---|
| 2009/0043250 A1 | 2/2009 | Gonnelli |
| 2009/0048536 A1 | 2/2009 | Freeman et al. |
| 2009/0054813 A1 | 2/2009 | Freeman et al. |
| 2009/0054971 A1 | 2/2009 | Mitsunaga et al. |
| 2009/0076453 A1 | 3/2009 | Mejlhede et al. |
| 2009/0088648 A1 | 4/2009 | Jaffe et al. |
| 2009/0099427 A1 | 4/2009 | Jina et al. |
| 2009/0099478 A1 | 4/2009 | Cassells et al. |
| 2009/0099529 A1 | 4/2009 | Anderson et al. |
| 2009/0101447 A1 | 4/2009 | Durham et al. |
| 2009/0105614 A1 | 4/2009 | Momose et al. |
| 2009/0118662 A1 | 5/2009 | Schnall |
| 2009/0124994 A1 | 5/2009 | Roe |
| 2009/0130646 A1 | 5/2009 | Fletcher et al. |
| 2009/0131829 A1 | 5/2009 | Freeman et al. |
| 2009/0155838 A1 | 6/2009 | Hale |
| 2009/0182306 A1 | 7/2009 | Lee et al. |
| 2009/0187117 A1 | 7/2009 | Imai |
| 2009/0187160 A1 | 7/2009 | McAllister et al. |
| 2009/0187167 A1 | 7/2009 | Sexton et al. |
| 2009/0198189 A1 | 8/2009 | Simons et al. |
| 2009/0198215 A1 | 8/2009 | Chong et al. |
| 2009/0206158 A1 | 8/2009 | Thuries et al. |
| 2009/0209883 A1 | 8/2009 | Higgins et al. |
| 2009/0215159 A1 | 8/2009 | Kirby |
| 2009/0216103 A1 | 8/2009 | Brister et al. |
| 2009/0216629 A1 | 8/2009 | James et al. |
| 2009/0264720 A1 | 10/2009 | Torjman et al. |
| 2009/0270792 A1 | 10/2009 | Lastovich et al. |
| 2009/0315684 A1 | 12/2009 | Sacco et al. |
| 2009/0318779 A1 | 12/2009 | Tran |
| 2009/0318846 A1 | 12/2009 | Prausnitz et al. |
| 2010/0010374 A1 | 1/2010 | Escutia et al. |
| 2010/0021947 A1 | 1/2010 | Emery et al. |
| 2010/0030111 A1 | 2/2010 | Perriere |
| 2010/0042137 A1 | 2/2010 | Oronsky et al. |
| 2010/0049126 A1 | 2/2010 | Bronfeld et al. |
| 2010/0069726 A1 | 3/2010 | Levinson |
| 2010/0069730 A1 | 3/2010 | Bergstrom et al. |
| 2010/0094170 A1 | 4/2010 | Wilson et al. |
| 2010/0111970 A1 | 5/2010 | Pons et al. |
| 2010/0114014 A1 | 5/2010 | Roser |
| 2010/0121368 A1 | 5/2010 | Kim et al. |
| 2010/0147763 A1 | 6/2010 | Tsou et al. |
| 2010/0160894 A1 | 6/2010 | Julian et al. |
| 2010/0210970 A1 | 8/2010 | Horikawa et al. |
| 2010/0222703 A1 | 9/2010 | Takashima et al. |
| 2010/0234768 A1 | 9/2010 | Uchiyama et al. |
| 2010/0240079 A1 | 9/2010 | Jackson |
| 2010/0249560 A1 | 9/2010 | Levinson et al. |
| 2010/0256465 A1 | 10/2010 | Bernstein et al. |
| 2010/0256524 A1 | 10/2010 | Levinson et al. |
| 2010/0261988 A1 | 10/2010 | Tamir |
| 2010/0269837 A1 | 10/2010 | Levinson et al. |
| 2010/0272652 A1 | 10/2010 | Levinson et al. |
| 2010/0282834 A1 | 11/2010 | Devergne |
| 2010/0292191 A1 | 11/2010 | Mainx et al. |
| 2010/0318111 A1 | 12/2010 | Sarna et al. |
| 2010/0324449 A1 | 12/2010 | Rostaing et al. |
| 2010/0324451 A1 | 12/2010 | Hiroko et al. |
| 2011/0003770 A1 | 1/2011 | Eek |
| 2011/0009847 A1 | 1/2011 | Levinson et al. |
| 2011/0034830 A1 | 2/2011 | Nakamura et al. |
| 2011/0040208 A1 | 2/2011 | Mcminn et al. |
| 2011/0040317 A1 | 2/2011 | Lee et al. |
| 2011/0105828 A1 | 5/2011 | Perless et al. |
| 2011/0105872 A1 | 5/2011 | Chickering et al. |
| 2011/0105951 A1 | 5/2011 | Bernstein et al. |
| 2011/0105952 A1 | 5/2011 | Bernstein et al. |
| 2011/0112384 A1 | 5/2011 | Eisenhardt et al. |
| 2011/0112438 A1 | 5/2011 | Radzuinas et al. |
| 2011/0125058 A1 | 5/2011 | Levinson et al. |
| 2011/0137203 A1 | 6/2011 | Nishiuchi et al. |
| 2011/0172508 A1 | 7/2011 | Chickering, III et al. |
| 2011/0172510 A1 | 7/2011 | Chickering, III et al. |
| 2011/0181410 A1 | 7/2011 | Levinson et al. |
| 2011/0245708 A1 | 10/2011 | Finkel et al. |
| 2011/0251562 A1 | 10/2011 | Chickering, III et al. |
| 2011/0276027 A1 | 11/2011 | Trautman et al. |
| 2011/0282173 A1 | 11/2011 | Fonduca et al. |
| 2011/0288389 A9 | 11/2011 | Levinson et al. |
| 2011/0306853 A1 | 12/2011 | Black et al. |
| 2012/0010529 A1 | 1/2012 | Chickering, III et al. |
| 2012/0016308 A1 | 1/2012 | Schott |
| 2012/0039809 A1 | 2/2012 | Levinson et al. |
| 2012/0041338 A1 | 2/2012 | Chickering et al. |
| 2012/0089050 A1 | 4/2012 | Fukuda |
| 2012/0123297 A1 | 5/2012 | Brancazio |
| 2012/0184906 A1 | 7/2012 | McAllister |
| 2012/0271125 A1 | 10/2012 | Bernstein et al. |
| 2012/0275955 A1 | 11/2012 | Haghgooie et al. |
| 2012/0277629 A1 | 11/2012 | Bernstein et al. |
| 2012/0277696 A1 | 11/2012 | Gonzalez-Zugasti et al. |
| 2012/0277697 A1 | 11/2012 | Haghgooie et al. |
| 2012/0315271 A1 | 12/2012 | Shelton et al. |
| 2013/0018279 A1 | 1/2013 | Plante et al. |
| 2013/0079666 A1 | 3/2013 | Gonzalez-Zugasti et al. |
| 2013/0081960 A1 | 4/2013 | Schott |
| 2013/0131741 A1 | 5/2013 | Kourtis et al. |
| 2013/0138058 A9 | 5/2013 | Chickering, III et al. |
| 2013/0158468 A1 | 6/2013 | Bernstein et al. |
| 2013/0158482 A1 | 6/2013 | Davis et al. |
| 2014/0336536 A1 | 11/2014 | Brancazio |
| 2015/0038876 A1 | 2/2015 | Gonzalez-Zugasti et al. |
| 2015/0057510 A1 | 2/2015 | Levinson et al. |
| 2015/0087944 A1 | 3/2015 | Levinson et al. |
| 2015/0157787 A1 | 6/2015 | Cully et al. |
| 2015/0278476 A1 | 10/2015 | Levinson et al. |
| 2015/0313522 A1 | 11/2015 | Bernstein et al. |
| 2015/0320349 A1 | 11/2015 | Haghgooie et al. |
| 2015/0342509 A1 | 12/2015 | Peeters et al. |
| 2016/0038068 A1 | 2/2016 | Chickering et al. |
| 2016/0262676 A1 | 9/2016 | Haghgooie et al. |
| 2017/0067803 A1 | 3/2017 | Jackson et al. |
| 2017/0120022 A1 | 5/2017 | Chickering et al. |
| 2017/0120023 A1 | 5/2017 | Davis et al. |
| 2017/0127990 A1 | 5/2017 | Levinson et al. |
| 2017/0127991 A1 | 5/2017 | Bernstein et al. |
| 2017/0172481 A1 | 6/2017 | Berthier et al. |
| 2017/0215790 A1 | 8/2017 | Levinson et al. |
| 2017/0224264 A1 | 8/2017 | Brancazio |
| 2017/0281852 A1 | 10/2017 | Bernstein et al. |
| 2018/0008183 A1 | 1/2018 | Chickering et al. |
| 2018/0132774 A1 | 5/2018 | Gonzalez-Zugasti et al. |
| 2018/0242890 A1 | 8/2018 | Chickering et al. |
| 2018/0310884 A1 | 11/2018 | Chickering et al. |
| 2018/0317829 A9 | 11/2018 | Gonzalez-Zugasti et al. |
| 2019/0023473 A1 | 1/2019 | Schott |
| 2019/0053740 A1 | 2/2019 | Davis et al. |
| 2019/0159709 A1 | 5/2019 | Barone et al. |
| 2019/0209820 A1 | 7/2019 | Chickering et al. |
| 2019/0216380 A1 | 7/2019 | Ivosevic et al. |
| 2019/0336058 A1 | 11/2019 | Haghgooie et al. |
| 2020/0015751 A9 | 1/2020 | Chickering et al. |
| 2020/0353155 A1 | 11/2020 | Bernstein et al. |
| 2021/0022681 A1 | 1/2021 | Chickering et al. |

FOREIGN PATENT DOCUMENTS

| | | |
|---|---|---|
| CN | 2331315 Y | 8/1999 |
| CN | 2462854 Y | 12/2001 |
| CN | 2600055 Y | 1/2004 |
| CN | 1499949 A | 5/2004 |
| CN | 1501788 A | 6/2004 |
| CN | 1524493 A | 9/2004 |
| CN | 1551743 A | 12/2004 |
| CN | 1753646 A | 3/2006 |
| CN | 101248998 A | 8/2008 |
| CN | 101347384 A | 1/2009 |
| CN | 101678196 A | 3/2010 |
| DE | 198 33 868 A1 | 5/2000 |
| DE | 20 2008 010918 U1 | 12/2008 |
| EP | 0 043 738 A2 | 1/1982 |
| EP | 0 115 388 A1 | 8/1984 |

(56) References Cited

FOREIGN PATENT DOCUMENTS

| | | |
|---|---|---|
| EP | 0 250 693 A1 | 1/1988 |
| EP | 0 365 196 A2 | 4/1990 |
| EP | 0 535 266 A1 | 4/1993 |
| EP | 0 555 554 A1 | 8/1993 |
| EP | 0 803 288 A2 | 10/1997 |
| EP | 0 838 232 A2 | 4/1998 |
| EP | 0 977 032 A1 | 2/2000 |
| EP | 1 027 864 A1 | 8/2000 |
| EP | 1 360 934 A1 | 11/2003 |
| EP | 1 437 093 A1 | 7/2004 |
| EP | 1 470 781 A2 | 10/2004 |
| EP | 1 491 143 A1 | 12/2004 |
| EP | 1 522 260 A1 | 4/2005 |
| EP | 1 611 837 A2 | 1/2006 |
| EP | 1 639 938 A1 | 3/2006 |
| EP | 1 652 551 A2 | 5/2006 |
| EP | 1 834 589 A2 | 9/2007 |
| EP | 1 844 710 B1 | 10/2007 |
| EP | 1 997 431 A1 | 12/2008 |
| EP | 2 064 993 A1 | 6/2009 |
| EP | 2 077 128 A1 | 7/2009 |
| EP | 1 187 653 B1 | 3/2010 |
| EP | 2 701 601 A1 | 3/2014 |
| EP | 3087919 A1 | 11/2016 |
| FR | 2929135 A1 | 10/2009 |
| GB | 2 153 223 A | 8/1985 |
| JP | 61-198061 A2 | 9/1986 |
| JP | 63-108264 A | 5/1988 |
| JP | 03-060645 A2 | 3/1991 |
| JP | 4-053536 A2 | 2/1992 |
| JP | 5-63506 A | 8/1993 |
| JP | 06-508286 T2 | 9/1994 |
| JP | 7-255706 A | 10/1995 |
| JP | H08-080291 A | 3/1996 |
| JP | 2000-116629 A | 4/2000 |
| JP | 2002-085384 | 3/2002 |
| JP | 2002-272710 A | 9/2002 |
| JP | 2002-532165 A1 | 10/2002 |
| JP | 2003-159238 A | 6/2003 |
| JP | 2004-8413 A | 1/2004 |
| JP | 2004-500948 | 1/2004 |
| JP | 2004-191336 A | 7/2004 |
| JP | 2004-532079 A | 10/2004 |
| JP | 2005-011364 A | 1/2005 |
| JP | 2005-517463 A | 6/2005 |
| JP | 2005-522243 | 7/2005 |
| JP | 2005-211189 A | 8/2005 |
| JP | 2005-525141 A | 8/2005 |
| JP | 2005-245705 A | 9/2005 |
| JP | 2006-014789 | 1/2006 |
| JP | 2006-15148 A | 1/2006 |
| JP | 2006-109894 A | 4/2006 |
| JP | 2006-521555 A | 9/2006 |
| JP | 2006-280912 A | 10/2006 |
| JP | 2007-209549 A | 8/2007 |
| JP | 2007-209747 A | 8/2007 |
| JP | 2007-236686 | 9/2007 |
| JP | 2007-526460 A | 9/2007 |
| JP | 2008-022988 A | 2/2008 |
| JP | 2008-54884 A | 3/2008 |
| JP | 2008-079853 A | 4/2008 |
| JP | 2008-99988 A | 5/2008 |
| JP | 2008-099992 A | 5/2008 |
| JP | 2008-518662 A | 6/2008 |
| JP | 2008-534192 A | 8/2008 |
| JP | 2009-504273 A | 2/2009 |
| JP | 2009-509679 A | 3/2009 |
| JP | 2009-066385 A | 4/2009 |
| JP | 2009-078173 A | 4/2009 |
| JP | 2009-519064 A | 5/2009 |
| JP | 2009-254899 A2 | 8/2009 |
| JP | 2010-520036 A | 6/2010 |
| JP | 2011-511660 A | 4/2011 |
| JP | 2011-522593 A | 8/2011 |
| JP | 2014-516645 A | 7/2014 |
| KR | 2003-0061753 A | 7/2003 |
| WO | 92/02175 A1 | 2/1992 |
| WO | 92/04867 A1 | 4/1992 |
| WO | 93/00043 A1 | 1/1993 |
| WO | 95/10223 A2 | 4/1995 |
| WO | 95/15783 A1 | 6/1995 |
| WO | 97/08987 A1 | 3/1997 |
| WO | 97/10745 A1 | 3/1997 |
| WO | 97/034587 A2 | 9/1997 |
| WO | 97/48442 A1 | 12/1997 |
| WO | 98/24366 A2 | 6/1998 |
| WO | 99/27852 A1 | 6/1999 |
| WO | 99/59657 A1 | 11/1999 |
| WO | 00/35357 A1 | 6/2000 |
| WO | 00/35530 A1 | 6/2000 |
| WO | 00/74763 A2 | 12/2000 |
| WO | 01/43643 A1 | 6/2001 |
| WO | 01/93946 A1 | 12/2001 |
| WO | 02/00101 A2 | 1/2002 |
| WO | 02/05890 A2 | 1/2002 |
| WO | WO 02/30301 A1 | 4/2002 |
| WO | WO 02/30506 A2 | 4/2002 |
| WO | WO 02/078533 A2 | 10/2002 |
| WO | WO 02/091922 A1 | 11/2002 |
| WO | WO 02/100253 A2 | 12/2002 |
| WO | WO 02/100460 A2 | 12/2002 |
| WO | WO 02/101359 A2 | 12/2002 |
| WO | WO 03/020134 A2 | 3/2003 |
| WO | WO 03/026611 A2 | 4/2003 |
| WO | WO 03/030984 A1 | 4/2003 |
| WO | WO 03/037407 A1 | 5/2003 |
| WO | WO 03/039632 A2 | 5/2003 |
| WO | WO 2003/037403 A1 | 5/2003 |
| WO | WO 03/070099 A1 | 8/2003 |
| WO | WO 03/082091 A2 | 10/2003 |
| WO | WO 03/088851 A1 | 10/2003 |
| WO | WO 2003/083469 A2 | 10/2003 |
| WO | WO 03/099123 A1 | 12/2003 |
| WO | WO 04/006982 A3 | 1/2004 |
| WO | WO 04/022133 A2 | 3/2004 |
| WO | WO 04/085995 A2 | 10/2004 |
| WO | WO 2005/000118 A1 | 1/2005 |
| WO | WO 2005/023111 A1 | 3/2005 |
| WO | WO 2005/025413 A2 | 3/2005 |
| WO | WO 2005/084534 A1 | 9/2005 |
| WO | WO 2005/095965 A1 | 10/2005 |
| WO | WO 2005/107594 A2 | 11/2005 |
| WO | WO 2005/123173 A2 | 12/2005 |
| WO | WO 2006/003403 A1 | 1/2006 |
| WO | WO 2006/019823 A2 | 2/2006 |
| WO | WO 2006/027586 A1 | 3/2006 |
| WO | WO 2006/050032 A2 | 5/2006 |
| WO | WO 2006/105968 A1 | 10/2006 |
| WO | WO 2006/111741 A1 | 10/2006 |
| WO | WO 2006/121510 A2 | 11/2006 |
| WO | WO 2006/128034 A1 | 11/2006 |
| WO | WO 2006/132504 A2 | 12/2006 |
| WO | WO 2007/002521 A2 | 1/2007 |
| WO | WO 2007/002522 A1 | 1/2007 |
| WO | WO 2007/021979 A2 | 2/2007 |
| WO | WO 2007/073870 A2 | 7/2007 |
| WO | WO 2007/079530 A1 | 7/2007 |
| WO | WO 2007/091671 A1 | 8/2007 |
| WO | WO 2007/092585 A2 | 8/2007 |
| WO | WO 2007/097754 A1 | 8/2007 |
| WO | WO 2007/108519 A1 | 9/2007 |
| WO | WO 2007/108987 A1 | 9/2007 |
| WO | WO 2007/115291 A2 | 10/2007 |
| WO | WO 2007/124411 A1 | 11/2007 |
| WO | WO 2008/016646 A2 | 2/2008 |
| WO | WO 2008/031035 A2 | 3/2008 |
| WO | WO 2008/043156 A1 | 4/2008 |
| WO | WO 2008/052034 A1 | 5/2008 |
| WO | WO 2008/062032 A1 | 5/2008 |
| WO | WO 2008/081444 A2 | 7/2008 |
| WO | WO 2008/109845 A2 | 9/2008 |
| WO | WO 2008/153930 A1 | 12/2008 |
| WO | WO 2009/004627 A3 | 1/2009 |
| WO | WO 2009/008267 A1 | 1/2009 |

(56) References Cited

FOREIGN PATENT DOCUMENTS

| WO | WO 2009/011138 A1 | 1/2009 |
|---|---|---|
| WO | WO 2009/027950 A2 | 3/2009 |
| WO | WO 2009/055693 A2 | 4/2009 |
| WO | WO 2009/071775 A1 | 6/2009 |
| WO | WO 2009/101112 A1 | 8/2009 |
| WO | WO 2009/104765 A1 | 8/2009 |
| WO | WO 2009/107135 A2 | 9/2009 |
| WO | WO 2009/126653 A1 | 10/2009 |
| WO | WO 2009/145920 A1 | 12/2009 |
| WO | WO 2009/148624 A1 | 12/2009 |
| WO | WO 2009/149308 A2 | 12/2009 |
| WO | WO 2009/151421 A1 | 12/2009 |
| WO | WO 2010/011641 A2 | 1/2010 |
| WO | WO 2010/101620 A2 | 9/2010 |
| WO | WO 2010/101621 A1 | 9/2010 |
| WO | WO 2010/101625 A2 | 9/2010 |
| WO | WO 2010/101626 A1 | 9/2010 |
| WO | WO 2010/110916 A2 | 9/2010 |
| WO | WO 2010/120294 A1 | 10/2010 |
| WO | WO 2011/016019 A1 | 2/2011 |
| WO | WO 2011/053796 A2 | 5/2011 |
| WO | WO 2011/065972 A2 | 6/2011 |
| WO | WO 2011/088214 A2 | 7/2011 |
| WO | WO 2012/058337 A2 | 5/2012 |
| WO | WO 2012/064802 A1 | 5/2012 |
| WO | WO 2012/149134 A1 | 11/2012 |
| WO | WO 2014/160893 A2 | 10/2014 |
| WO | WO 2017/191221 A1 | 11/2017 |

OTHER PUBLICATIONS

International Preliminary Report on Patentability for PCT/US2011/047581 dated Feb. 28, 2013.
[No Author Listed] Air-Tite Products Co., Inc.—LuerLock. Oct. 14, 2008. Retrieved from the Internet: https://web.archive.org/web/20081023203858/https://www.air-tite-shop.com/c-7-luer-lock.aspx on Aug. 28, 2019. 2 pages.
[No Author Listed] Air-Tite Products Co., Inc.—Luer Slip. Oct. 14, 2008. Retrieved from the Internet: https://web.archive.org/web/20081014224752/https://www.air-tite-shop.com/c-6-luer-slip.aspx on Aug. 28, 2019. 2 pages.
[No Author Listed] Greiner Bio-One Preanalytics Catalogue. www.gbo.com/preanalytics. Feb. 2012, 76 pages.
[No Author Listed] Safe-T-Fill®: 100% Plastic Capillary Blood Collection Systems. RAM Scientific. [Month of publication not listed on copy] 2003. Last accessed Jun. 28, 2012 at http//www.ramsci.com.
[No Author Listed] Sof-Tact Manual. Date Unknown. 57 pages. (After reasonable inquiry, the undersigned believes this manual was available beginning 2001, but cannot determine the exact date of this publication. The year of publication is sufficiently earlier than the effective U.S. filing date and priority date so that the particular month and year of publication is not in issue. See MPEP 609.04(a).).
[No Author Listed], Whatman Neonatal Screening Cards-Capabilities. GE Healthcare. Dec. 2009; 12 pages, www.gelifesciences.com/whatman.
Angell et al., Silicon Micromechanical Devices. Scientific American. Apr. 1983;248:44-55.
Aungst et al., Contributions of drug solubilization, partitioning, barrier disruption, and solvent permeation to the enhancement of skin permeation of various compounds with fatty acids and amines. Pharm Res. Jul. 1990;7(7):712-8.
Baroli, Penetration of metallic nanoparticles in human full-thickness skin. J. Ind. Derm. 2007;127:1701-12. Epub Mar. 22, 2007.
Bina et al., Clinical impact of prandial state, exercise, and site preparation on the equivalence of alternative-site blood glucose testing. Diabetes Care. Apr. 2003;26(4):981-5.
Brown, Encapsulation of glucose oxidase and an oxygen-quenched fluorophore in polyelectrolyte-coated calcium alginate microspheres as optical glucose sensor systems. Biosens Bioelec. 2005;21:212-16. Epub Sep. 17, 2004.
Cormier et al., Transdermal delivery of desmopressin using a coated microneedle array patch system. J Control Release. Jul. 7, 2004;97(3):503-11.
Duffy et al., Rapid Prototyping of Microfluidic Systems and Polydimethylsiloxane. Anal Chem. Dec. 1, 1998;70:4974-84.
Elias, The Microscopic Structure of the Epidermis and Its Derivatives. In: Percutaneous Absorption-Mechanisms-Methodology. Bronaugh et al., eds. Marcell Dekker. 1989;3-12. (The year of publication is sufficiently earlier than the effective U.S. filing date and any foreign priority date so that the particular month of publication is not in issue. See MPEP 609.04(a)).
Fineberg et al., Use of an automated device for alternative site blood glucose monitoring. Diabetes Care. Jul. 2001;24(7):1217-20.
Fuhrer et al., Building a Smart Hospital using RFID technologies: Use Cases and Implementation. 2006; 14 pages.
Gomes et al., Evaluation of nanoparticles loaded with benzopsoralen in rat peritoneal exudate cells. Int J Pharm. Mar. 6, 2007;332(1-2):153-60. Epub Sep. 27, 2006.
Kost et al., Chapter 4. Ultrasound-Mediated Transdermal Drug Delivery. In: Topical Drug Bioavailability Bioequivalance, and Penetration. Shah et al., eds. Plennum, NY. 1993:91-104. (The year of publication is sufficiently earlier than the effective U.S. filing date and any foreign priority date so that the particular month of publication is not in issue. See MPEP 609.04(a)).
Matriano et al., Macroflux microprojection array patch technology: a new and efficient approach for intracutaneous immunization. Pharm Res. Jan. 2002;19(1):63-70.
McShane, Microcapsules as 'smart tattoo' glucose sensors: engineering systems with enzymes and glucose-binding sensing elements, Top Fluor. Spec., 2006, vol. 11, Glc. Sens., p. 131-163. (The year of publication is sufficiently earlier than the effective U.S. filing date and any foreign priority date so that the particular month of publication is not in issue. See MPEP 609.04(a)).
Mitragotri et al., Sonophoresis: Enhanced Transdermal Drug Delivery by Application of Ultrasound. In: Encl. of Pharm. Tech., vol. 14, Swarbrick, J., Boylan, J., (Eds.), vol. 14, 103-122, 1996. (After reasonable inquiry, the undersigned believes this was available in 1996, but cannot determine the exact date of this publication. The year of publication is sufficiently earlier than the effective U.S. filing date and priority date so that the particular month and year of publication is not in issue. See MPEP 609.04(a).).
Rousche et al., A method for pneumatically inserting an array of penetrating electrodes into cortical tissue. Annals of Biomedical Engineering. Jul. 1992;20(4):413-22.
Rousche et al., A System for Impact Insertion of a 100 Electrode Array into Cortical Tissue. Annual Intl Conf IEEE Engineer Med Biol Soc. 1990; 12(2):O494-95. (The year of publication is sufficiently earlier than the effective U.S. filing date and any foreign priority date so that the particular month of publication is not in issue. See MPEP 609.04(a)).
Rouse, Effects of mechanical flexion on the penetration of fullerene amino acid-derivatized peptide nanoparticles through skin. Nano Lett. Jan. 2007;7(1): 155-60. Epub Dec. 6, 2006.
Suk et al., Gene delivery to differentiated neurotypic cells with RGD and HIV Tat peptide functionalized polymeric nanoparticles. Biomaterials. Oct. 2006;27(29):5143-50.
Uhrich, Polymeric systems for controlled drug release. Chem. Rev. 1999;99:3181-98. Epub Oct. 26, 1999.
Verbaan et al., Improved piercing of microneedle arrays in dermatomed human skin by an impact insertion method. J Control Release. May 22, 2008;128(1):80-8. Epub Feb. 26, 2008.
Whitesides et al., Soft lithography in biology and biochemistry. Annu Rev Biomed Eng. Aug. 2001;3:335-73.
Xia et al., Soft Lithography. Ann Rev Mater Sci. Aug. 1998;28:153-84.
Matsuura et al., Development of a blood extraction device for a miniature SMBG system. Dec. 27, 2007. Proceedings vol. 6799, BioMEMS and Nanotechnology III; 67990N (2007) https://doi.org/10.1117/12.758869. Event: SPIE Microelectronics, MEMS, and Nanotechnology, 2007, Canberra, ACT, Australia.

\* cited by examiner

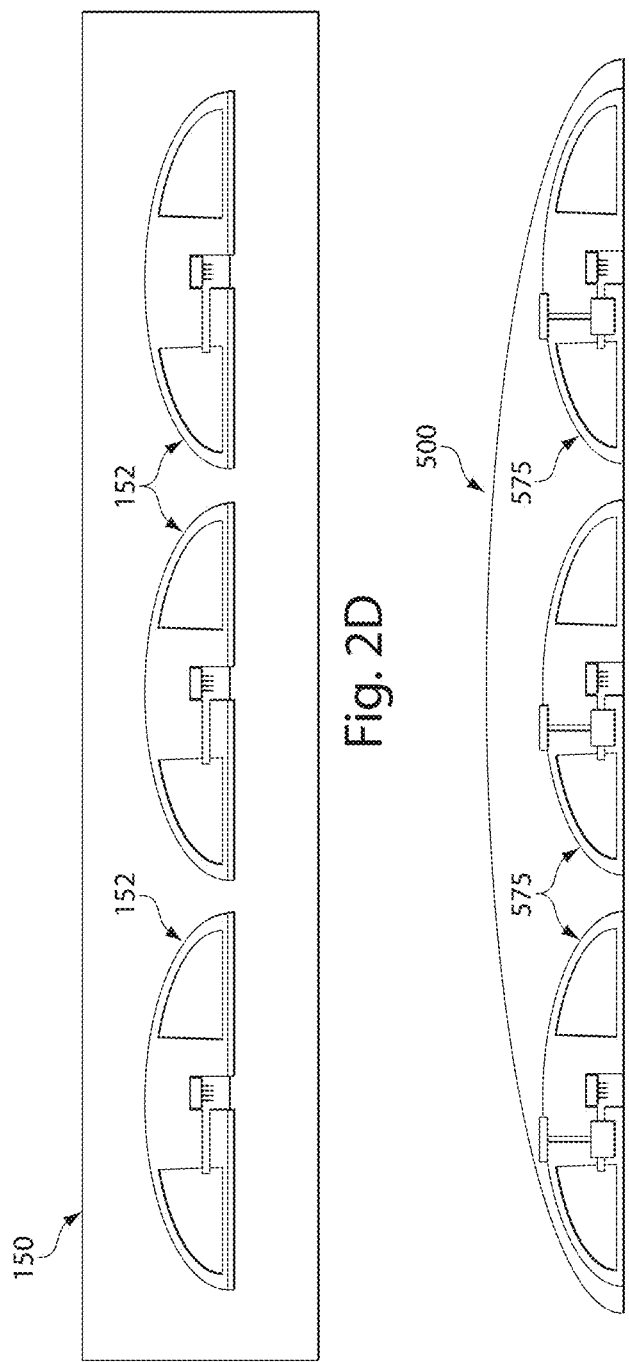

SYSTEMS AND TECHNIQUES FOR MONITORING SUBJECTS

RELATED APPLICATIONS

This application is a continuation of U.S. patent application Ser. No. 13/208,808, filed Aug. 12, 2011, entitled "Systems and Techniques for Monitoring Subjects," by Levinson, et al., which claims the benefit of U.S. Provisional Patent Application Ser. No. 61/373,757, filed Aug. 13, 2010, entitled "Systems and Techniques for Monitoring Subjects," by Levinson, et al., each of which is incorporated herein by reference.

FIELD OF INVENTION

The present invention generally relates to systems and methods for monitoring and/or providing feedback for drugs or other pharmaceuticals taken by a subject.

BACKGROUND

One problem often faced by physicians and other health care providers is that drugs and other pharmaceuticals that are prescribed to subjects are not taken by the subjects, or are not taken properly by the subjects. The reasons for non-compliance or poor compliance vary, and include forgetfulness, cost, inconvenience, lack of follow-up, and fear of taking medications. Accordingly, techniques for monitoring or improving compliance are needed.

SUMMARY OF THE INVENTION

The present invention generally relates to systems and methods for monitoring and/or providing feedback for drugs or other pharmaceuticals taken by a subject. The subject matter of the present invention involves, in some cases, interrelated products, alternative solutions to a particular problem, and/or a plurality of different uses of one or more systems and/or articles.

In one aspect, the present invention is generally directed to a device. In some embodiments, the device includes a sensor able to determine or evaluate a species (e.g., a sample of fluid, tissue, blood, etc.) withdrawn from a subject, and an indicator able to indicate an external reward based on the determination of the species. In another set of embodiments, the device includes means for determining a species withdrawn from a subject, and means for providing an external reward based on the determination of the species.

In accordance with some embodiments, the device includes a sensor able to determine an amount and/or concentration of a species withdrawn from a subject, and a component able to produce non-number feedback or other information related to the amount or concentration of the species.

The present invention, in another aspect, is directed to a method. According to some embodiments, the method includes acts of determining a species withdrawn from a subject using a device fastened to the subject, and providing an external reward based on a presence or concentration of the species. In another set of embodiments, the method includes acts of determining a species withdrawn from a subject, on multiple days, using one or more devices able to be fastened to the skin, and providing an external reward based on the number of determinations. The method, in yet another set of embodiments, includes acts of determining an amount and/or concentration of a species withdrawn from a subject using a device fastened to the subject, and producing non-number feedback indicative of the determination of the species.

In some embodiments, the method includes acts of determining information relating to a species withdrawn from a subject, transmitting the information to a computer, and causing the computer to provide feedback to the subject based on the information relating to the species. In another set of embodiments, the method includes acts of receiving information obtained from a subject representing a property of a species withdrawn from the subject, and presenting an external reward to a user based on the received data. The method, in still another set of embodiments, includes acts of determining information representing a property of a species withdrawn from a subject using a device fastened to the subject, and transmitting the information to a machine capable of causing an external reward to be presented to a user of the machine.

The method, according to one set of embodiments, includes acts of administering a drug to a subject, determining a species withdrawn from a subject that is indicative of the drug administered to the subject, and providing feedback to the subject regarding the species. In some embodiments, the drug administered to the subject is not distinguishable from a placebo by the subject without any external equipment.

In yet another set of embodiments, the method includes acts of administering a drug to a subject having a condition suspected of being treatable by the drug, determining a species withdrawn from a subject that is indicative of the drug administered to the subject, and providing feedback to the subject regarding the species. In some cases, the drug does not cause a measurable change to the condition of the subject within the first 24 hours after administering the drug.

In one aspect, the present invention is generally directed to a device-implemented method. In some embodiments, the method includes acts of applying a device to a subject, where the device is able to obtain a physical measurement from the subject, and based on obtaining the measurement, effecting a financial transaction with the device.

The method, in certain embodiments, includes acts of applying a device to a subject, wherein the device is able to obtain an invasive physical measurement from the subject, and based on obtaining the measurement, recommending a medical treatment with the device.

In certain embodiments, the method includes acts of applying a device to a subject, where the device is able to obtain an invasive physical measurement from the subject, and based on obtaining the measurement, performing a medical treatment on the subject using the device.

According to some embodiments, the method includes acts of applying a device to a subject, where the device is able to obtain an invasive physical measurement from the subject, and based on obtaining the measurement, delivering a drug to the subject using the device.

The method, in some embodiments, includes acts of receiving medical data from a subject in a device, determining positional data of the subject in the device, and producing composite data comprising the medical data and the positional data using the device.

The method, in yet other embodiments, includes acts of determining a species withdrawn from a subject using a device fastened to the subject, and providing an external reward to a person other than the subject based on a concentration of the species.

In some embodiments, the method includes acts of injecting a tracer into a subject using a device comprising a plurality of microneedles, and tracking movement of the subject by remote monitoring of the tracer.

In certain embodiments, the method includes acts of injecting a population of subjects with tracers using devices each comprising microneedles, and determining a characteristic of the population of subjects by determining the tracers within the population of subjects.

In another aspect, the present invention is generally directed to a device. According to certain embodiments, the device includes a fluid transporter able to withdraw fluid from a subject, a sensor able to determine an analyte suspected of being present within the withdrawn fluid and configured to receive the withdrawn fluid, and a transmitter responsive to the sensor and able to effect a financial transaction as a function of the sensor's determination.

The device, according to some embodiments, includes a fluid transporter able to withdraw fluid from a subject, a sensor able to determine an analyte suspected of being present within the fluid, a processor able to determine a drug treatment based at least in part on the sensor determination, and a reservoir for containing a drug deliverable to the subject based on the processor determination.

In accordance with some embodiments, the device includes a sensor able to determine a species withdrawn from a subject, and a device indicator able to indicate an external reward based on the determination of the species.

In another aspect, the present invention encompasses methods of making one or more of the embodiments described herein. In another aspect, the present invention encompasses methods of using one or more of the embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 2D illustrates a kit containing more than one device, in yet another embodiment of the invention;

FIG. 2E illustrates a device according to still another embodiment of the invention;

DETAILED DESCRIPTION

Figure 1A:
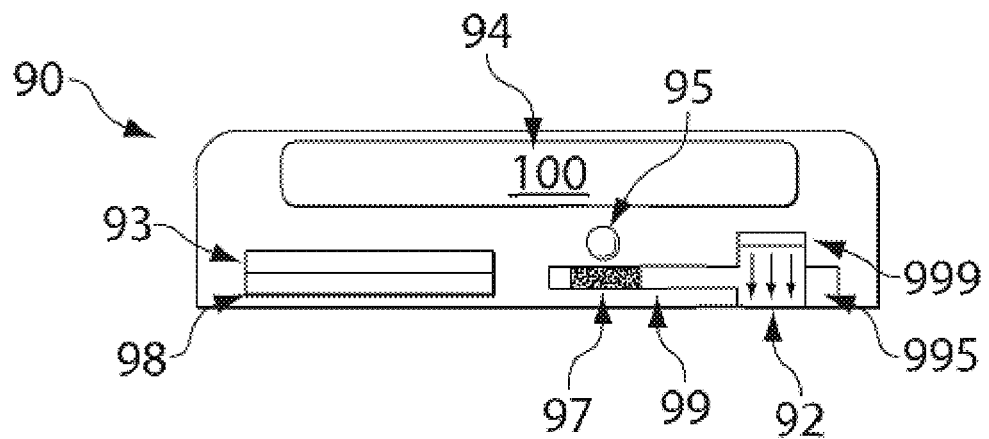
FIG. 1A-1B illustrate devices according to certain embodiments of the invention.

The present invention generally relates to systems and methods for monitoring and/or providing feedback for drugs or other pharmaceuticals taken by a subject. In certain embodiments, feedback to the subject, or to other personnel, may take the form of visual and/or audible displays, or financial rewards or incentives. Examples include coupons, memberships, cash, or the like. Some embodiments are generally directed to devices for monitoring a subject, and in some cases, engaging in financial transactions related to the condition of the subject, for example, transmitting insurance claims, charging a financial account, recording payments, or the like. In certain embodiments, the monitoring may take the form of medical monitoring. For example, in response to a condition of the subject, a device may transmit or display data or information relating to the condition of the subject to the subject, and/or to other personnel such as relatives, friends, or medical personnel, who could then take appropriate actions depending on the condition of the subject. In some cases, the device itself may also be able to perform medical treatments, for example, by delivering a drug or other pharmaceutical agent to the subject, e.g., such as is described herein. For example, the device may be able to deliver a hormone, a protein, a small molecule, etc., to the subject, and/or the device may begin monitoring other analytes within the blood (or other fluid). In some cases, the device may be used to deliver an electric charge or shock to the subject as part of the medical treatment. In some cases, the device may also transmit other data concerning the subject, for example, the location of the subject, or vital factors relating to the subject (e.g., the subject's temperature or blood pressure).

Some embodiments of the invention are directed to populations of individuals, e.g., where a population of individuals is tracked to determine a condition of the population. For example, blood from a population of individuals may be obtained using various devices such as those described herein, and data based on the blood samples may be used, for example, to track the spread of a disease. In some cases, such samples may be obtained without knowledge by the individuals. Thus, in certain embodiments, one or more individuals may be tracked covertly. For example, an individual may be tracked to determine his or her location, for instance, by obtaining a blood sample from the individual, and/or by injecting a tracer in the individual that can be later detected (e.g., remotely, or using a covertly obtained blood sample from that individual). Thus, for instance, the location of an individual may be determined by studying an analyte within the blood that is indicative of the location of the individual, or tracers may be covertly applied at one location to individuals at that location to determine if the subject in question had been through that location. Examples of these are discussed in detail below.

In one aspect, the present invention is directed to devices and methods for determining a species within the skin of a subject, and producing feedback to a subject based on the determination of the species. The feedback may be, for example, visual, audible, tactile, a change in temperature, etc. In some cases, information regarding the determination of the species may be transmitted to another entity, e.g., a health care provider, a computer, a relative, etc., which may then provide feedback to the subject in some fashion. In some cases, the feedback may be directly indicative of the species, e.g., whether the species is present, the concentration of the species, whether a by-product of a reaction involving the species is present, whether a compound affected by the species is present, etc. However, the feedback may also be indirect in some embodiments. For example, the subject may be presented with an external reward, e.g., based on the determination of the species within the skin. For instance, a reward such as cash, coupons, songs, discounts, personal items, etc., may be offered based on the level of compliance of the subject. Still other aspects of the invention are generally directed to kits involving such devices (with or without the drug to be monitored), methods of promoting such systems, or the like.

In one aspect, the present invention is generally directed to devices able to monitor or provide feedback to a subject taking a drug or other pharmaceutical, and/or to other personnel. For example, feedback may be provided to a relative of the subject, a caregiver for the subject, medical personnel caring for the subject (e.g., a nurse, a doctor, etc.), or the like. Thus, in certain embodiments, feedback may be provided to anyone who would communicate such feedback to the subject. The feedback given to the subject may be based on information regarding the determination of the drug or other pharmaceutical, for example, an amount and/or concentration of the drug or other pharmaceutical within the subject. For instance, the feedback may include information regarding the subject's compliance with taking one or more drugs or other pharmaceutical compositions. Depending on the personnel, additional information may be given to the subject, e.g., warnings about compliance (or lack thereof), information about potential drug interactions, suggestions for improving compliance, suggestions for changes in lifestyle, or the like.

The species to be determined within the subject may be present anywhere within the subject, e.g., within the skin of the subject, and/or within other bodily fluids such as blood or interstitial fluid. The species may be an administered composition (e.g., a drug or other pharmaceutical), and/or another species that is related to the composition, such as a tracer or other compound taken with the administered compound, for example, such as the systems and methods disclosed in U.S. Pat. Apl. Ser. No. 61/163,733, filed Mar. 26, 2009, entitled "Determination of Tracers within Subjects," by Douglas A. Levinson (incorporated by reference herein in its entirety). For example, the species to be determined may be the product of an interaction of the drug (or other pharmaceutical) with the subject. As specific non-limiting examples, the species may be a metabolite of the administered composition, a product or by-product of the administered composition with the subject (for example, a cleavage product), a marker for a disease that is treatable by the administered composition (for instance, a protein, a hormone, a small molecule, etc.), a species within the body that the administered composition interacts with (e.g., degrades), such as a target of the administered composition (for example, a protein or enzymatic target within the subject), or the like. Accordingly, in the description herein, it should be understood that references to determining the drug (or other pharmaceutical or other administered composition) in the subject (e.g., in the skin, blood, interstitial fluid, etc. of the subject) are by way of example only, and in other embodiments, other species related to the administered composition may be determined in any suitable location within the subject, instead of or in addition to the administered composition, such as those described herein.

In certain embodiments, the device is able to interrogate a portion of a subject, for example, a blood sample taken from the subject, and in response, initiate or effect a financial transaction, or recommend or perform a medical treatment on the subject. In some cases, the interrogation is invasive. For instance, the interrogation may involve the insertion of an object into a subject, and/or the receiving of a substance (such as blood) from the subject. In contrast, measurements such as measuring temperature or blood pressure are not invasive since there is no insertion and/or receiving of a substance into or out of the skin (or beneath the skin) of the subject.

For example, the financial transaction may be performed directly by the device, and/or the device may interface with another device able to perform the financial transaction. The financial transaction may be associated with the actions taken by the device, and/or based on an analyte determined by the device. For example, a financial transaction may occur every time the device is used (e.g., every time the device delivers and/or receives a substance to or from the subject), every time a drug is delivered by the device, every time an assay is performed by the device, on a regular basis (e.g., akin to rent), or the like. The financial transaction may be a charge to a credit card, a charge card, a credit account, a bank account, a debit account, an insurance account, or the like. In some embodiments, the device may cause an insurance claim or a claim against the government (e.g., for social security, Medicare, Medicaid, etc.) to be entered.

In some embodiments, the device comprises a transmitter able to conduct a financial transaction. For example, the transmitter may be able to access a wireless system to conduct the financial transaction, e.g., using established procedures, or the device may be plugged into a transmitter in order to process the financial transaction. The device may also contain a processor for recommending and/or for performing a medical treatment. In some cases, the processor may include a database, e.g., of drug information and/or other kinds of suitable medical treatment. For instance, the processor may be able to determine, via one or more sensors, an analyte suspected of being present in blood or other fluid received from a subject, and based on the analyte, take some action, for example, sending a signal (e.g., to the subject or other personnel, e.g., to a doctor), or in some cases, activating an actuator, e.g., for delivering a drug or other pharmaceutical to the subject. As an example, the device may inject a drug into the subject using one or more microneedles or other fluid transporters or substance transfer components, based on sensor readings of a fluid such as blood received from the subject.

Figure 5A:
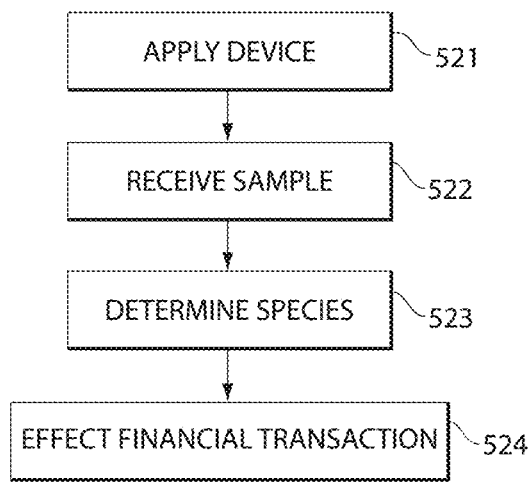
FIGS. 5A-5D illustrate various methods, in accordance with certain embodiments of the invention.

A non-limiting example of such a process is now described with respect to the flowchart shown in FIG. 5A. In this figure, a device is applied to a subject 521, e.g., by the subject (i.e., self-administered) or another person (e.g., a health care provider). The device is then activated (or in some cases, self-activated) to withdraw or receive fluid or other sample 522 from the subject, e.g., blood, interstitial fluid, etc. The device may then analyze the fluid to determine one or more species 523, e.g., using one or more sensors as discussed herein. In some cases, analysis of the species occurs on the device itself. Based on this determination, the device may effect a financial transaction 524. For example, the financial transaction may include transmitting insurance claims, charging a financial account, recording payments, or the like. The financial transaction may also include a charge to a credit card, a charge card, a credit account, a bank account, a debit account, an insurance account, or the like. In some embodiments, the financial transaction may be an insurance claim or a claim against the government. Other suitable financial transactions are discussed herein.

Figure 4:
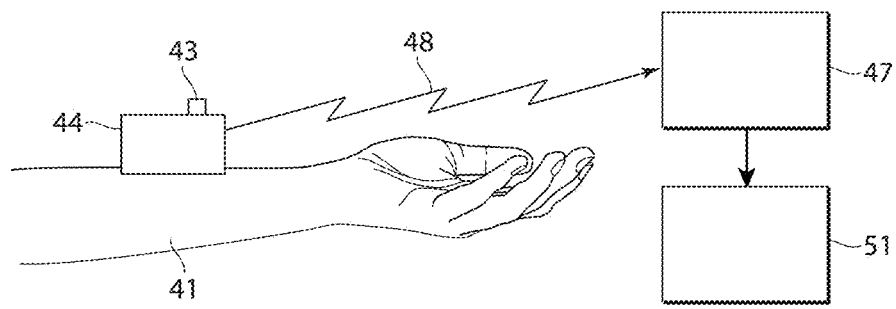
FIG. 4 is a schematic diagram illustrating a device transmitting information about a species from a subject to a device able to offer a reward, in accordance with one embodiment of the invention.
Figure 5B:
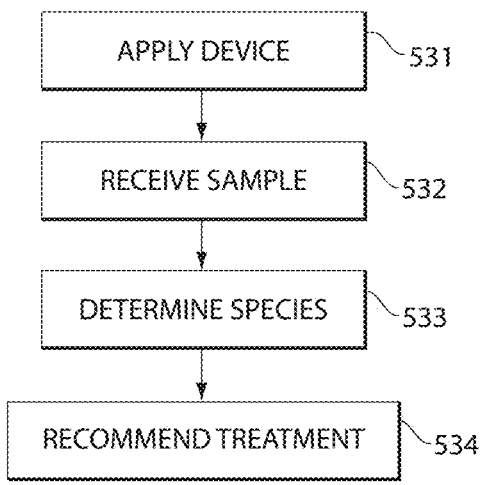
Figure 5C:
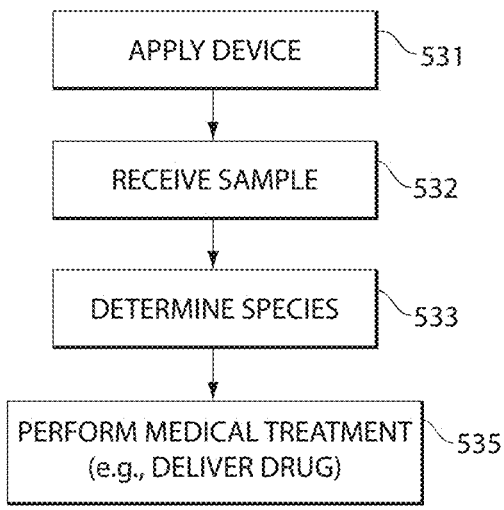

A non-limiting example of a process for recommending a medical treatment is shown in the flowchart in FIG. 5B In this figure, a device is applied to a subject 531, e.g., by the subject (i.e., self-administered) or another person (e.g., a health care provider). The device is then activated (or in some cases, self-activated) to withdraw or receive fluid or other sample 532 from the subject, e.g., blood, interstitial fluid, etc. The device may then analyze the fluid to determine one or more species 533, e.g., using one or more sensors as discussed herein. In some cases, analysis of the species occurs on the device itself. Based on this determination, the device may recommend a medical treatment. For example, the device may include a database of potential treatments, and determination of the species from 533 may be used to select a suitable medical treatment, e.g., for display by the device, and/or for by display by an output device, for instance, output device 51 in FIG. 4. For instance, the medical treatment may be to continue taking a drug or other pharmaceutical agent (or to stop taking the drug or other pharmaceutical), to increase or decrease the dosage of the drug or other pharmaceutical, to take another drug or other pharmaceutical agent, to avoid taking certain drugs or other pharmaceutical agents (e.g., in the case of adverse drug interactions), to eat or avoid eating certain foods (e.g., containing sugar, or foods implicated in allergic reactions), to rest or sleep, to see a doctor or other medical personnel, etc. FIG. 5C is a similar example flowchart, except the device may be able to perform a suitable medical treatment in 535, e.g., by delivering a drug or other pharmaceutical agent to the subject.

Feedback from the device may be provided in any suitable form. As mentioned, feedback may be provided to the subject, or to other personnel. In some cases, the feedback may be directly provided by the device, e.g., to the subject after determination of the species. In certain embodiments, the feedback may be auditory, visual, olfactory, tactile, thermal, or the like.

For example, if the feedback is auditory, the feedback may include sounds such as jingles, songs, music, sound effects, or the like. In some cases, the sounds may be selectable by the subject or other personnel. For instance, the subject may select a first song indicating compliance, and a second song (or no song) indicating non-compliance; the subject may also select additional songs in some embodiments for other indications (e.g., partial compliance, a reminder to take the composition, a song indicating successful compliance over some predetermined period of time or number of administrations, etc.). Sound may be produced by a device using any suitable technique, for example, using a speaker or a relay clicker. Techniques for causing a speaker to play music or sounds will be familiar to those of ordinary skill in the art. For example, the speaker may be a digital speaker that plays songs stored in a memory device, e.g., in any suitable format (e.g., flash memory, magnetic tape, hard drive memory, optical media such as CDs or DVDs, or the like). Other types of sounds may be used in other embodiments, for example, sound effects (e.g., beeps, buzzes, jingles, etc.), synthesized sounds or speech, verbal reminders, or the like.

As another example, the feedback may be tactile or temperature (e.g., such that the subject senses a change in temperature of the device). One non-limiting example of a tactile sensation is a change in temperature (e.g., getting warmer or cooler), for example, using electronic heating or cooling devices such as resistive heaters or Peltier coolers. Thus, as a particular example, a device may be worn that produces heat or cooling when compliance is lacking, thereby reminding the wearer to administer the drug or other pharmaceutical. As other examples of tactile feedback, the device may vibrate, tighten or loosen, etc. to indicate certain conditions. For instance, the device may be worn around the arm (e.g., as in a bracelet or wristwatch), and the device may tighten around the arm if the subject has not been compliant.

In some embodiments, the feedback may be visual. For example, the device may include one or more lights, LEDs, LCDs, a screen able to display an image, or the like. As a specific non-limiting example, lights may be provided that are red when compliance is lacking and green if the subject exhibits adequate compliance. In some cases, the lights may also flash, e.g., to get attention. Other lights may be provide in other embodiments, for example, to indicate that the next administration is due, to indicate operation of the device, to indicate successful compliance over some predetermined period of time or number of administrations, etc. As another example, a light within the device may be used to produce a logo or an advertisement when the composition has been taken, etc. In some cases, the feedback may be non-number based, i.e., the feedback does not include the display of numbers, but instead contains other methods or symbols to indicate feedback, e.g., lights, bars, plots, signals, graphs, logos, or the like. As still another example, the device may display numbers, a series of lights, pictograms, LEDs, LCDs, logos, etc., indicating information regarding the species within the subject, for example, the concentration, the number of times the drug or other pharmaceutical was taken by the subject, the time since the last administration of the drug or other pharmaceutical was previously administered, the time before the next administration, or the like. If a screen is used, the screen may be able to display arbitrary information, e.g., regarding operation of the device, information regarding the species within the subject, information regarding administration of the drug or other pharmaceutical, weblinks, or other useful information, etc. In still another embodiments, the device may produce a desirable display of lights, logos, advertisements, movies, etc., as a reward for successful compliance.

These may also be combined in still other embodiments. For example, the device may produce a movie with sounds to indicate compliance (or lack thereof), the device may produce blinking lights during or following a song, or the like.

In certain embodiments, the feedback that is provided by the device may be related to the drug or other pharmaceutical in some way. For example, the feedback may indicate whether the drug (or other pharmaceutical) was taken or not, the degree of compliance, the concentration of a species within the subject (measured directly or indirectly, e.g., by determining a metabolite within the subject), the time since the drug was taken, the time until the next administration of the drug, the number of administrations, etc. In some of embodiments, the feedback may be a reward indicating some degree of successful compliance. For example, feedback may be provided after the subject has taken the drug, after the subject has taken the drug a certain number of times, after the subject has taken the drug for a certain period of time, once a certain concentration of a species within subject has been reached, or the like. The feedback may be numerical and/or non-numerical. Such feedback may, in some embodiments, be of sufficient value to the subject that the subject may behave in a certain way, e.g., increasing compliance or continuing taking the drug or other pharmaceutical. In other embodiments, as discussed herein, the feedback may include a reward, such as an external reward. The reward may also influence the subject's behavior in some cases.

In some cases, feedback may be provided to the subject in real time, e.g., by the use of a graph, numbers, lights, etc. As a particular example, the device may display a number that indicates the concentration of a species within the subject (e.g., glucose), and optionally, when a certain concentration is reached, the device may also indicate to the subject in some fashion that a medication (e.g., insulin) is needed, for example, by activating a light, displaying a logo, playing a sound or a song, or the like.

The device may be used once, or multiple times. For instance, in some embodiments, the device may be used to determine a species within the skin at multiple points of time, e.g., on multiple days, or even continuously in some instances. Feedback may be provided to the subject immediately or within a short time after determining the species, and/or information regarding the species may be stored for later use (e.g., as discussed below). For instance, in certain embodiments, after the subject has taken the drug a certain number of times, or after a certain number of days, feedback may be provided to the subject, for example, in the form of a reward as discussed below.

As discussed, in some embodiments, feedback is provided by the device itself. However, in other embodiments, feedback may be provided by another entity. The entity may be another person (such as a relative, medical personnel, etc.), or a non-living entity, such as a computer or an Internet-based service. For example, information about the species may be transmitted to the other entity, which may then provide feedback to the subject in a suitable fashion.

In some embodiments, the device may transmit information regarding the subject and/or administration of the drug or other pharmaceutical to another entity. The information may be transmitted, e.g., wirelessly (for example, using radio antennas, transceivers, infrared light, laser light, visible light, acoustic energy, or the like), or through the use of wires (for example, using electronic ports such as parallel ports, serial ports, USB connections, RS232/485 communication transceivers, 4-20 mA analog transceivers, an Ethernet transceiver, or the like). Any suitable transmission protocol may be used, e.g., Bluetooth, Wi-Fi or IEEE 802.11, WiMax, peer-to-peer networking, Wireless FireWire, or the like. The information may be transmitted relatively quickly after determination of a species within the subject, and/or the information may be stored for later transmission and/or retrieval, for example, by the subject, or by another person.

If information is stored on the device, any suitable technique may be used to store such information, e.g., in a data storage compartment, for example, silicon integrated circuits, magnetic media, optical media, or other kinds of data storage devices. In one embodiment, the data storage component includes a computer-readable medium, for example, a medium that stores information through electronic properties, magnetic properties, optical properties, etc. of the medium. Examples of computer-readable media include, but are not limited to, silicon and other semiconductor microchips or integrated circuits, radio frequency tags or circuits, compact discs (e.g., in CD-R or CD-RW formats), digital versatile discs (e.g., in DVD+R, DVD-R, DVD+RW, or DVD-RW formats), insertable memory devices (e.g., memory cards, memory chips, memory sticks, memory plugs, etc.), "flash" memory, magnetic media (e.g., magnetic strips, magnetic tape, DATs, tape cartridges, etc.), floppy disks (e.g., 5.25 inch or 90 mm (3.5 inch) disks), optical disks, and the like. In some embodiments, the data storage component may be reversibly attached to and removed from the device. In some embodiments, the data storage component may be volatile, i.e., some power is required by the data storage component to maintain the data therein. In other embodiments, however, the data storage component is non-volatile. In some embodiments, the data storage component is an element that is constructed and arranged to allow data to be stored to and/or retrieved. In one embodiment, the memory or data storage component includes a data storage chip. As used herein, a "data storage chip" is a microchip or microprocessor to which data can be stored and/or retrieved. Typically, the data storage chip comprises a semiconductor and often contains electronic circuitry. In some cases, the data may include drug treatment data, medical treatment data, etc.

In some embodiments, information regarding the subject and/or administration of the drug or other pharmaceutical may be delivered to the subject or another person. For instance, the device may determine a species within the skin of a subject, then transmit the information regarding the species to another entity, e.g., a receiver, a computer, a web page on the Internet, etc., for retrieval and/or analysis by another person, e.g., the subject, a relative, medical personnel, etc. If another person is involved, the person may provide feedback to the subject. For example, the person could review information regarding the species, and/or make a determination regarding compliance of the subject with administration of the drug or other pharmaceutical. In some cases, the person may give advice (such as medical advice), warnings, encouragement, counseling, etc., to the subject regarding administration and/or compliance issues. In addition, as previously discussed, in some embodiments, additional information may also be given to the subject, for example, information about potential drug interactions, suggestions for changes in lifestyle, methods for improving compliance, changes in prescription, or the like.

Figure 5D:
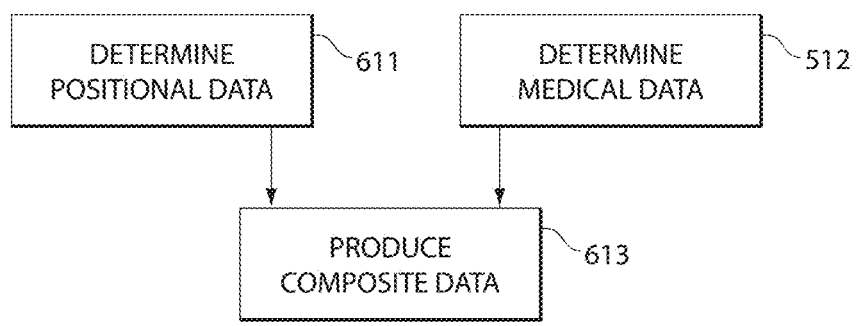

In some cases, the information may be combined with other information or data. For instance, information regarding the subject, e.g., regarding concentration of a species within the subject, and/or other medical information about the subject (e.g., the subject's temperature, blood pressure, oxygen levels, etc.) may be combined with other data, for example, indicating the time of day, the location of the subject, or the like. For instance, in certain embodiments, the location of the subject may be determined using GPS ("Global Positioning System") reception equipment, or other similar systems (e.g., Galileo, Beidou, COMPASS, GLONASS, IRNSS, QZSS, etc.). In some cases, a device may include a suitable receiver (e.g., a GPS receiver), and/or the device may be able to electronically interface with a separate receiver, e.g., one carried by the subject. Many types of receivers, e.g., for GPS, can be obtained commercially. The data may be combined to produce composite data that can be, for example, stored in memory, transmitted to another entity, displayed on a web page, or the like, e.g., as is described herein. An example is illustrated in the flowchart of FIG. 5D, where positional data 611 and medical data 512 are combined to produce composite data 613.

Thus, in some embodiments, the same device may be used to determine both positional data and medical data regarding the subject. In other embodiments, however, more than one device may be used. For example, a first device may determine medical data and a second device may determine positional data, then the data combined to produce the composite data (e.g., comprising at least the medical data and the positional data), either in the first device, the second device, or in some cases, in a third device.

In some embodiments, the device may indicate that the subject (or another person, as described herein) may have access to a web page. The device may have a device indicator that indicates access to the web page by any suitable technique, for example, visual, audible, tactile, a change in temperature, etc. As non-limiting examples, the device may turn on a light, display an image or a logo, to produce a sound, play a song, etc. to indicate that the web page is accessible, to indicate a change or an update in the content of the web page, produce a reminder to review the web page, etc.

The web page may be used to display information to the subject, and/or to another person. For instance, in certain embodiments, the device may transmit information to another entity (e.g., a computer), and the computer may produce a web page that can be accessed by the subject, or another person. In some cases, the web page may be a private or encrypted web page accessible only to the subject, and/or only to select individuals (e.g., certain doctors or other health care providers). The web page may display information relating to the species, other information of interest to or for the subject, or in some cases, the web page may be used to provide a reward to the subject, e.g., for sufficient compliance.

For example, the web page may, in some embodiments, display information relating, directly or indirectly, to the species. For example, the web page may display information regarding compliance or administration of the drug or other pharmaceutical by the subject, the concentration of a species in the subject (e.g., of the drug or other pharmaceutical, or a species related to the drug or other pharmaceutical, e.g., a metabolite, a target, a product, a by-product, a marker for a disease treatable by the drug or other pharmaceutical, etc.). As other examples, the web page may indicate whether the drug (or other pharmaceutical) was taken or not, the number of times it was taken by the subject, the degree of compliance, the concentration of a species within the subject (measured directly or indirectly, e.g., by determining a metabolite within the subject), the time since the drug was taken, the time until the next administration of the drug, the number of administrations, other health-related information (e.g., relating to the composition, for example, potential side effects, allergic reactions, interactions with other drugs, etc.), as well as past histories or one or more of these in some cases, or the like.

In some cases, the web page may display information of interest to or for the subject. As non-limiting examples, the web page may display information or advertising regarding the drug or other drugs of potential interest to or for the subject, health-related information, links to related web sites, or the like. As specific examples, the web page may include a link to an on-line "chat" with medical personnel who can answer questions that the subject may have regarding the subject's health, or the web page may provide counseling regarding improving compliance of the subject in taking the drug or other pharmaceutical.

In some embodiments, the web page may use information relating to the species to produce information, data, probabilities, etc., relating to the subject. For instance, the web page may indicate that, by successfully complying with a treatment for a certain period of time, the probability of an adverse event has been changed. As a specific example, the web page may report that, by successfully complying with treatment over a certain period of time, the probability of a heart attack has decreased by a certain percentage, the probability of an acute attack of a disease has decreased by a certain percentage, the life expectancy of the subject has increased by a certain amount, etc.

According to some embodiments, feedback provided to the subject may include a reward, e.g., upon achieving some level of successful compliance. For example, the feedback or reward may be provided after the subject has taken a drug (or other pharmaceutical), after the subject has taken the drug a certain number of times, after the subject has taken the drug for or after a certain period of time, once a certain concentration of a species within subject has been reached, or the like. In some cases, the reward may be one selected by the user; in other cases, the reward may be determined by another person, e.g., by a doctor or other health care provider, or the reward may be predetermined. For instance, as discussed below, in certain embodiments, a kit may be provided to the subject that includes a drug or other pharmaceutical, and a device able to determine the drug within the skin. The device may, in some cases, be preprogrammed to give a reward when a certain compliance by the subject is reached.

The reward may be any suitable reward. In some cases, the reward may be one determinable by the user. In some embodiments, the reward may be provided directly by the device. For instance, the device may display an image, play a song or music, display a pattern of lights, play a movie or a movie clip, etc., as a suitable reward to the subject. In some cases, however, the reward may be one that is external to the device, i.e., the reward is an "external reward." For example, the reward may be a monetary reward (e.g., cash, coupons, discounts, gift cards, etc.), physical merchandise (e.g., of a predetermined nature, or selectable by the user, etc.), downloadable content (e.g., sound files, game files, pictures, movies, etc.), or the like. As a specific non-limiting example, the reward may be one or more arbitrary "points," and when a certain number of points are reached, the subject may be given a reward, or the subject may be allowed to choose a reward from a number of potential rewards. In some cases, the subject may be able to acquire even more points (for example, for higher levels of compliance, longer periods of compliance, smaller fluctuations in the concentration of a species, etc.) and the ability to choose even larger or more valuable rewards. The reward may be selectable, for example, by access to a suitable web page (e.g., as discussed herein), by selecting an item from a physical or an electronic catalog, or the like.

Examples of coupons include, for instance, coupons to restaurants, hotels, cars, vacations, health clubs, or the like. Other examples of monetary or financial rewards include, but are not limited to, increased pay, discounts for prescriptions, memberships to health clubs, drug discount programs, loyalty cards, gift cards, changes in insurance premiums, or increased time off (e.g., increased vacation days), or the like. As additional examples, the external reward may take the form of e-mail or other electronic messages sent to the subject (or other entity), or electronic short messages such as Twitter posts or tweets. The messages may be in the form of congratulatory messages, status updates, encouragement, weblinks, or the like.

As previously discussed, feedback may be provided to the subject, or to persons other than the subject, for example, to a relative of the subject, a caregiver for the subject, medical personnel caring for the subject (e.g., a nurse, a doctor, etc.), or the like. The feedback may also include, for example, monetary or financial rewards (e.g., "kickbacks" for successful performance by the subject, changes in pay, bonuses, or the like).

In one aspect, the present invention is directed generally to devices able to monitor or provide feedback to a subject taking (or not taking) a drug or other pharmaceutical substance, and/or to provide such feedback to other personnel. For example, feedback may be provided to a relative of the subject, a caregiver for the subject, medical personnel caring for the subject (e.g., a nurse, a doctor, etc.), or the like. Thus, in one set of embodiments, feedback may be provided to anyone who would communicate such feedback to the subject. The subject is typically human, although the subject may be non-human in some cases. The feedback given to the subject may be based on information regarding the determination of the drug or other pharmaceutical substance, for example, an amount and/or concentration of the drug or other pharmaceutical substance within the subject. The determination may be qualitative (e.g., determining the presence or absence of the drug or other pharmaceutical substance) and/or quantitative (e.g., determining an amount and/or concentration, etc.). For instance, the feedback may include information regarding the subject's compliance with taking (or not taking) one or more drugs or other pharmaceutical substances. Depending on the personnel, additional information may be given to the subject, e.g., warnings about compliance (or lack thereof), information about potential drug interactions, suggestions for improving compliance, suggestions for changes in lifestyle, or the like.

Figure 3A:
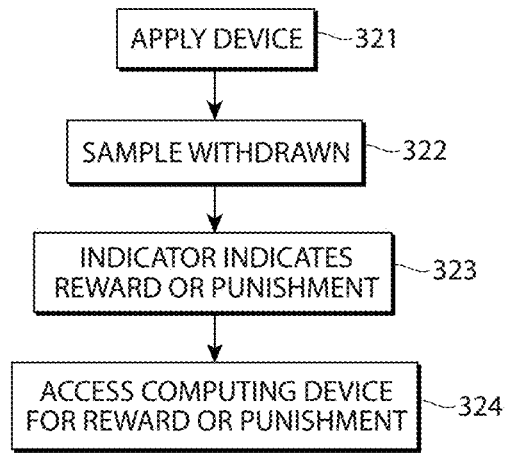
FIGS. 3A-3C illustrate certain methods in accordance with various embodiments of the invention.

A non-limiting example of such a process is now described with respect to the flowchart shown in FIG. 3A. In this figure, a device is applied to a subject 321, e.g., by the subject (i.e., self-administered) or another person (e.g., a health care provider). The device is then activated (or in some cases, self-activated) to withdraw or receive fluid 322 from the subject, e.g., blood, interstitial fluid, etc. The device may then analyze the fluid for one or more species, e.g., using one or more sensors as discussed herein. In some cases, analysis of the species occurs on the device itself. In certain instances, information about the species (e.g., the presence and/or absence, concentration, amount, etc.) is transmitted externally of the device, e.g., to a computing device, which may also in some embodiments return a signal to the device. After such analysis, if certain conditions are met, the device may activate an indicator 323 (e.g., light, sound, graphics, music, etc.) which alerts the subject (or another person) that an external reward or punishment is available. The subject (or another person) can then access a computing device 324 (which may be the same or different from the computing device discussed above) to access the external reward and/or to determine what punishment is to be applied. The computing device may, for example, display a weblink to access the reward or punishment, and/or there may be an output device able to output a reward (e.g., a coupon or a certificate).

Figure 3B:
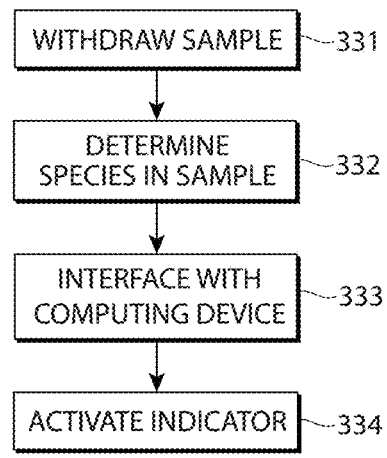

As illustrated in the non-limiting example of FIG. 3B, the device, in one set of embodiments, may be operated as follows. A sample may be withdrawn or received from a subject to which the device is applied 331. For example, the sample may be blood, interstitial fluid, or the like. The device then analyzes the sample 332 to determine one or more species within the sample, e.g., the presence and/or absence, amount, concentration, etc. For example, one or more sensors as discussed herein may be present within the device. In some cases, analysis of the species occurs on the device itself. In certain instances, the device interfaces with an external computing device 333 so that information about the species (e.g., the presence and/or absence, concentration, amount, etc.) can be transmitted externally of the device, e.g., to a computing device, which may also in some embodiments return a signal to the device. Based on such analysis, the device may then activate an indicator 334, for example, light, sound, graphics, music, etc. to alert the subject (or another person) that an external reward (or punishment) is available. In some cases, the device itself may perform the analysis of the species and activate the indicator, prior to interfacing with an external computing device.

Figure 3C:
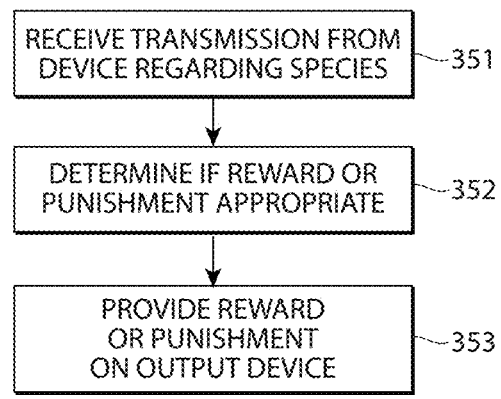

One non-limiting example method of using the computing device is now illustrated with respect to FIG. 3C. In this figure, an external computing device (e.g., a general purpose computer, a specially-built computer, an application-specific integrated circuit, a microprocessor, etc.) receives a transmission 351 from a device that is used to withdraw or receive a sample from a subject for analysis. The sample may be, for example, blood or interstitial fluid. For example, the device may include one or more sensors able to determine a species suspected of being present within the sample withdrawn or received from the subject, and the device may transmit sensor data, and/or the device may analyze sensor data and transmit information about the species (e.g., the presence or absence, amount, concentration, etc.) to the computing device. In this example, based on the transmission, the computing device may determine if a reward (or punishment) is appropriate 352, e.g., using criteria such as those described herein. Optionally, the computing device (or another computing device) may be used by the subject, or another person, to access an external reward or punishment 353. For example, the computing device may be a computer that a person can log into to receive the external reward. In some cases, the computer device may be connected to an output device for producing the external reward, e.g., a screen, a TV, a printer, a speaker, or the like.

A schematic illustration of another example system is shown in FIG. 4. In this figure, a device 44 for withdrawing or receiving a fluid is placed on a portion of a subject 41 (e.g., an arm or a leg), and in some cases, immobilized thereto (for example, using an adhesive). After withdrawing or receiving a sample from the subject (e.g., blood or interstitial fluid), device 44 determines one or more species suspected of being present within the sample using one or more sensors. Information from the sensors may be analyzed by device 44, and/or transmitted 48 to an external computing device 47. For example, device 44 may determine the presence of a species, and in some cases, determine if an external reward (or punishment) should be offered to the subject. If an external computing device is used, any method of transmission to the computing device may be used, including wireless or radio transmissions. In some embodiments, device 44 may also be able to determine positional data, e.g., if device 44 includes a GPS receiver, which may also be transmitted to external computing device 47.

In some cases, external computing device 47 may also send a signal back to device 44. For example, in some embodiments, external computing device 47 may be used to analyze the species and determine if an external reward (or punishment) should be offered to the subject. Thus, information about the species and/or whether such an external reward or punishment should be offered may be transmitted back to device 44.

If it is determined that the subject should be offered an external reward (or punishment), device 44 may activate a suitable indicator 43 to inform the subject (or another person). For example, indicator 43 may be include a display screen, a speaker, a light or an LED, or the like, e.g., as discussed herein. Computing device 47, and/or another output device 51, may then be used to offer the external reward (or punishment) to the subject (or other person). For example, the subject or other person may access computing device 47 and/or output device 51 to claim the reward or accept the punishment.

In some aspects, the systems described herein may be useful for any drug. In some cases, the drug may be one in which the benefit to the subject taking the drug is not necessarily immediate or apparent. For example, a drug able to treat anemia or decrease cholesterol levels may have benefits that are not immediately felt by the subject (e.g., an increase in red blood cell count or a decrease in the amount of cholesterol found in the blood). Thus, the subject taking the drug may not be aware of any immediate substantial benefit by taking the drug. In many cases, the subject is discouraged from taking the drug due to the lack of any positive feedback, i.e., beneficial effects, by taking the drug. In some instances, this may be compounded by drugs having one or more adverse side effects, i.e., the subject is immediately exposed to adverse side effects upon taking the drug, while the beneficial effects of taking the drug are not immediately apparent. Accordingly, it is a feature of certain embodiments of the invention to provide feedback systems for subjects taking drugs, including but not limited to drugs having benefits that are not necessarily immediate or apparent.

In some embodiments, the drug is one whose beneficial effects occur on the time scale of weeks, or drugs whose main actions do not occur until at least about a day. Examples of such drugs include, but are not limited to, drugs that treat anemia, drugs that lower cholesterol, or drugs that treat high blood pressure, drugs that treat arthritis, etc. Specific non-limiting examples are discussed below. In certain embodiments, the drug is one whose are quantified using analytical measurements of the subject (or samples taken from the subject). Often, such drugs have effects cannot be felt by a subject, or cannot be quantified by a subject without analytical measurements beyond a sense of "feeling good." Examples include, but are not limited to, drugs that lower cholesterol, drugs that treat anemia, or drugs that treat high blood pressure. In some cases, the drug administered to the subject is not distinguishable, by the subject and/or by others, from a placebo without any external equipment (e.g., blood testing). For instance, on a time scale of a day, 2 days, 3 days, a week, 2 weeks, 3 weeks, 4 weeks, etc., the drug is one that would not be distinguishable from a placebo by a typical subject taking the drug. For instance, the effects of the drug may take a long time to occur, and/or the symptoms treated by the drug may not be immediately identifiable by the subject (e.g., treatment of mild anemia) in the absence of any external equipment (e.g., to determine levels of circulating blood cells).

In certain embodiments, the subject may be one that has or is at risk for high levels of lipids within the blood, for example, cholesterol. In some cases, for example, the subject may have total blood cholesterol level of at least about 200 mg/dl, at least about 210 mg/dl, at least about 220 mg/dl, etc.; HDL cholesterol levels of less than about 50 mg/dl, less than about 40 mg/dl, less than about 30 mg/dl, etc.; and/or LDL cholesterol levels of at least about 130 mg/dl, at least about 140 mg/dl, at least about 150 mg/dl, etc. Drugs that a subject may take to reduce or lower cholesterol and/or other lipid levels include, but are not limited to, statins or HMG-CoA reductase inhibitors (e.g., mevastatin, atorvastatin, cerivastatin, fluvastatin, lovastatin, pitavastatin, pravastatin, rosuvastatin, simvastatin, and/or combinations of these and/or other compounds), resins (e.g., cholestyramine, colestipol, or colesevelam), fibrates (e.g., gemfibrozil, fenofibrate, clofibrate), or niacin, and these may be determined in a subject, e.g., in the blood. For instance, a reward may be presented to a subject after a certain number or frequency of positive results where a satisfactory level of a drug was determined within the subject.

In some embodiments, the subject may have or be at risk for anemia, for example, having a decrease in the number of red blood cells and/or hemoglobin. Drugs useful for treating anemia include, but are not limited to, iron supplements, folic acid, vitamin B-12, erythropoietin or the like.

The subject may have or be at risk for asthma in some embodiments. In some cases, the asthma may include occasional asthma attacks. Examples of drugs usefully for treating asthma include, but are not limited to, long-acting bronchodilators such as beta-2-adrenoceptor agonists, salmeterol, formoterol, bambuterol, or albuterol; steroids such as fluticasone or budesonide; or combinations of these and/or others.

The subject, in some embodiments, may have chronic obstructive pulmonary disease (COPD) or asthma. Examples of potentially useful drugs to treat conditions such as chronic obstructive pulmonary disease or asthma include, but are not limited to, beta-2 agonists such as salbutamol, albuterol, terbutaline, salmeterol, or formoterol; anticholinergics such as ipratropium or tiotropium; corticosteroids such as prednisone, fluticasone, budesonide, mometasone, or beclomethasone; theophylline; or phosphodiesterase-4 antagonists such as roflumilast or cilomilast. Combinations of these and/or other drugs may also be used in some cases.

In certain embodiments, the subject may have osteoporosis. The osteoporosis may be treatable by administering drugs such as estrogen, bisphosphonate, calcium, vitamin D, or raloxifene.

In some embodiments, the subject may have diabetes, and may need treatment, e.g., with insulin. Glucose may be determined in the blood of the subject to determine the subject's insulin need and/or compliance with taking insulin at prescribed times.

In some embodiments, the subject may suffer from various chronic heart diseases. Characteristics determinable to determine if the subject is taking suitable drugs include, but are not limited to, pulse rate, blood pressure, or blood measurements such as cholesterol, calcium, sodium, potassium, chloride, bicarbonate, blood urea nitrogen (BUN), magnesium, creatinine, or glucose. Rewards such as external rewards may be presented if certain goals are met for some or all of these.

In some embodiments, the subject may suffer from inflammatory or immune-mediated conditions that are subject to periodic "flare-ups" or acute attacks, and the subject accordingly needs to take drugs to control the frequency of such attacks. Examples include, but are not limited to, arthritis (e.g., rheumatoid arthritis, osteoarthritis, etc.).

In certain embodiments, the subject may be one who is trying to reduce addiction, e.g., to nicotine or ethanol. Accordingly, nicotine or ethanol may be determined in the subject to determine if or to what degree the subject has been able to reduce addiction. Additionally, feedback, e.g., in the form of external rewards, etc., may be useful in providing a positive environment for the subject to continue efforts at reducing the addiction. In some embodiments, the subject may be one who is trying to lose weight. Glucose or other food compounds (e.g., triglycerides, free amino acids, other sugars, etc.) may be determined within the subject, and optionally, feedback may be provided, to the subject based on the determination of such compounds.

In some embodiments of the invention, as noted above, a species may be determined indirectly, for example, using a tracer of the species. As used herein, a "tracer" is a substance that can be determined within a subject, typically upon interaction with a tracer indicator. In some cases, the tracer is determinable in some fashion, e.g., by a sensor as disclosed herein. For example, the tracer may be radioactive or fluorescent in some cases; although in other cases, the tracer may not be radioactive and/or fluorescent. The determinable change in the tracer and/or the tracer indicator may be a visual change such as a change in appearance (e.g., color), a change in temperature, a change in sensation, or the like. The tracer itself may be any suitable compound that can be administered to the subject. In some cases, the determinable change may be determinable using suitable instrumentation.

In some cases, the tracer is chosen to have relatively little biological activity, and can be determined mainly by its interaction with the tracer indicator. However, in other cases, the tracer may have some biological activity. For instance, the amount of biological activity of the tracer within the subject may be predictable. As an example, a tracer may be cleared by the kidneys from the bloodstream at a certain rate, and by determining the concentration of tracer within the subject, e.g., by determining a change in a determinable property in a tracer indicator, and correcting for the clearance rate of the tracer, the pharmacokinetic activity of the tracer within the subject may be determined, and used to determine the pharmacokinetic activity of a substance administered to the subject. Usually, the tracer is produced externally or exogenously, then administered to the subject as discussed below. Non-limiting examples of tracers include certain proteins or carbohydrates such as inulin, or small molecules (typically less than about 1000 Da) such as creatinine.

As a non-limiting example, the tracer may exhibit substantially the same pharmacokinetic activity as the substance, or at least exhibit certain pharmacokinetic activities indicative of the substance. For instance, the tracer may exhibit similar absorption and/or distribution rates within the body, the same duration within the body, the same metabolism within the body, or the same excretion rates from the body, e.g., through the urine. In other cases, however, the tracer and the substance may exhibit substantially different pharmacokinetic parameters. For example, the tracer may exhibit substantially slower or faster absorption or distribution within the body. However, by determining the tracer, e.g., using a tracer indicator, an estimate of the pharmacokinetic activity of the substance within the body may still be obtained. In one embodiment, it may be sufficient to simply determine whether the tracer is present or absent in the body, and then infer that the substance is also present or absent in the body based on the tracer (for example, if the subject is given a composition that comprises both the tracer and the substance to be administered as a single entity). In some cases, the amount of tracer delivered to the subject may also be controlled in some fashion, for example, such that the certain pharmacokinetic activities of the tracer are substantially similar to the pharmacokinetic activities of the substance also administered to the subject. As non-limiting examples, the substance may be an alcoholic beverage or a drug that is administered with a tracer, and the tracer indicator used to determine whether the subject has indeed taken the substance or not.

In some aspects, a tracer may be determined in the skin of the subject, or a bodily fluid such as blood or interstitial fluid may be received from a subject and the tracer determined within the received fluid, thereby indicating the presence and/or amount of tracer within the subject. Thus, in some embodiments, a tracer may be determined in association with the subject, i.e., the tracer may be determined while the tracer is physically within the subject, e.g., within the skin of the subject, and/or the tracer may be determined after being removed from the subject in some fashion, e.g., by being received within a bodily fluid such as blood or interstitial fluid. The tracer is typically, but need not be, an auxiliary species administered along with the substance, the presence and/or quantity of which is to be determined in association with the subject, and in many cases the tracer has no purpose in relation to the subject other than its function as a tracer.

An "tracer indicator" is a species that exhibits a change in a determinable property upon interaction with a tracer. However, it should be understood that a tracer indicator is not necessarily required in all embodiments of the invention. In some cases, the tracer itself is determinable in some fashion. For example, the tracer may be radioactive or fluorescent in some cases, although in other cases, the tracer may not be radioactive and/or fluorescent. The determinable change in the tracer and/or the tracer indicator may be a visual change such as a change in appearance (e.g., color), a change in temperature, a change in sensation, or the like. The tracer itself may be any suitable compound that can be administered to the subject. In some cases, the determinable change may be one that can be determined by a human without the use of any equipment, for example, visually, tactilely, or the like. In other cases, however, the determinable change may be determinable using suitable instrumentation.

In some cases, the tracer is chosen to have relatively little, or essentially no, biological activity, and can be determined mainly by its interaction with the tracer indicator. However, in other cases, the tracer may have some biological activity. For instance, the amount of biological activity of the tracer within the subject may be predictable. As an example, a tracer may be cleared by the kidneys from the bloodstream at a certain rate, and by determining the concentration of tracer within the subject, e.g., by determining a change in a determinable property in a tracer indicator, and correcting for the clearance rate of the tracer, the pharmacokinetic activity of the tracer within the subject may be determined, and used to determine the pharmacokinetic activity of a substance administered to the subject. Usually, the tracer is produced externally or exogenously, then administered to the subject as discussed below. Non-limiting examples of tracers include certain proteins or carbohydrates such as inulin, or small molecules (typically less than about 1000 Da) such as creatinine. The tracer may be relatively non-toxic in some cases. In certain embodiments, the tracer is a molecule that has a relatively high rate of clearance from the body. For instance, the half-life of the tracer within the body may be less than about 3 days, less than about 2 days, less than about 1 day, less than about 18 hours, less than about 12 hours, less than about 9 hours, less than about 3 hours, or less than about 1 hour. In some cases, the tracer may include poly(ethylene) glycol, for example, PEG 300, PEG 400, PEG 2000, PEG 3350, or PEG 8000 (where "PEG" stands for poly(ethylene) glycol and the number indicates the molecular weight).

As a non-limiting example, the tracer may exhibit substantially the same pharmacokinetic activity as the substance, or at least exhibit certain pharmacokinetic activities indicative of the substance. For instance, the tracer may exhibit similar absorption and/or distribution rates within the body, the same duration within the body, the same metabolism within the body, or the same excretion rates from the body, e.g., through the urine. In other cases, however, the tracer and the substance may exhibit substantially different pharmacokinetic parameters. For example, the tracer may exhibit substantially slower or faster absorption or distribution within the body. However, by determining the tracer, e.g., using a tracer indicator, an estimate of the pharmacokinetic activity of the substance within the body may still be obtained. In one embodiment, it may be sufficient to simply determine whether the tracer is present or absent in the body, and then infer that the substance is also present or absent in the body based on the tracer (for example, if the subject is given a composition that comprises both the tracer and the substance to be administered as a single entity). In some cases, the amount of tracer delivered to the subject may also be controlled in some fashion, for example, such that the certain pharmacokinetic activities of the tracer are substantially similar to the pharmacokinetic activities of the substance also administered to the subject. The substance may be any substance to be delivered to a subject, in which a determination of the substance within the subject is desired. As non-limiting examples, the substance may be an alcoholic beverage or a drug that is administered with a tracer, and the tracer indicator used to determine whether the subject has indeed taken the substance or not. For example, the subject may be one who has trouble with memory; by visually determining a tracer indicator (e.g., in the skin), whether the tracer (and thus, the substance) has been administered (or self-administered) to the subject may be determined.

The tracer may be administered to the subject using any suitable method. For example, the tracer may be administered orally, vaginally, rectally, buccally, pulmonary, topically, nasally, transdermally, through parenteral injection or implantation, via surgical administration, or any other suitable method of administration. The tracer may be delivered systemically, or in some cases locally, e.g., at a site proximate a tracer indicator. The tracer may also be administered by the subject (i.e., self-administered), or offered and/or administered to the subject by someone else, e.g., a doctor or a nurse. In addition, techniques discussed below that may be useful for delivering a tracer indicator to a subject may also be useful for delivering a tracer to the subject. As discussed, the tracer and the tracer indicator need not be delivered using the same route of administration (although they can be), and they also need not be delivered simultaneously. For example, the tracer indicator may be rubbed onto the surface of the skin or injected into the skin, while the tracer may be delivered orally, or injected into the bloodstream of the subject.

The tracer may interact with a tracer indicator within the subject. As mentioned, a tracer indicator is a species that can interact with the tracer and exhibit a change in a determinable property upon such an interaction. For instance, the tracer indicator may change appearance or colors in the presence or in the absence of the tracer, e.g., the tracer indicator may exhibit a first color at a first concentration of the tracer and a second color at a second concentration of the tracer, or the tracer may exhibit a range of colors depending on the concentration of the tracer. The tracer indicator may, in certain cases, be immobilized within the subject, e.g., within a depot in the skin. For instance, the tracer indicator may be immobilized such that at least about 90% or at least about 95% of the tracer indicator administered to the subject stays in the location in which it was administered. In some cases, the change can be determined by a human without the use of any equipment. Non-limiting examples include changes in appearance (e.g., color), temperature changes, chemical reactions (e.g., capsaicin) which can be sensed by the subject (e.g., as a feeling of pain), or the like. Examples of capsaicin and capsaicin-like molecules include, but are not limited to, dihydrocapsaicin, nordihydrocapsaicin, homodihydrocapsaicin, homocapsaicin, or nonivamide.

As additional examples, the tracer indicator may include antibodies, enzymes, indicator dyes, or the like which are able to interact with a tracer, and which may exhibit a change in a determinable property, such as a change in color or aggregation, upon such an interaction. As a non-limiting example, in one embodiment, a tracer indicator comprising an antibody may bind to a tracer (e.g., inulin), and upon binding, aggregation of antibodies (e.g., multiple antibodies to the same target, primary antibodies and secondary antibodies where the secondary antibody is labeled, etc.) may be used to determine the tracer. Those of ordinary skill in the art will know of techniques for raising tracer indicators such as antibodies against a specific target.

In one aspect, the invention is generally directed to methods for administering a tracer or other compound to a subject, remotely and/or without their knowledge, even in cases where the subject is conscious or not asleep. For example, a tracer may be injected into a subject using a device as discussed herein, or other device. In some cases, for example, the device may be relatively small and unobtrusive, and/or produce minimal pain or sensation such that the subject is not conscious of the device's actions. For example, a fluid or a tracer may be injected to the subject using one or more microneedles as discussed herein. Examples of devices having such microneedles are disclosed herein; additional examples may be seen in a U.S. application being filed on even date herewith, entitled "Clinical and/or Consumer Techniques and Devices"; and in U.S. Apl. Ser. No. 61/373,764, entitled "Clinical and/or Consumer Techniques and Devices," each of which is incorporated herein by reference in its entirety.

The tracer may then be subsequently determined to determine the subject. For example, in certain embodiments, the tracer is covertly applied to a subject, without the subject's knowledge, and the tracer used to determine movements of the subject. As a specific non-limiting example, it can be determined whether or not the subject passed a certain location (and thus was subjected to the tracer). For example, the subject may pass a first location, where the tracer is covertly applied to the subject, then the subject may be tested at a second location, wherein the presence of the tracer is covertly determined, e.g., by covertly receiving blood from the subject using a device such as is described herein. If the subject passed the first location, the tracer will be detected in the blood of the subject at the second location; however, if the subject never passed the first location (e.g., the subject used a different route), then no tracer will be detected in the blood of the subject at the second location. Thus, movement of the subject may be tracked by monitoring the tracer within the subject.

In some embodiments, the tracer is used to determine a condition, such as a medical condition, of the subject, for example dehydration. The tracer may be, for example, an inert compound (e.g., inulin), a fluorescent compound, or the like, and may be determined by any suitable technique, e.g., fluorescence, urine samples, or the like. Additional examples of tracers also include proteins or carbohydrates such as inulin, or small molecules (typically less than about 1000 Da) such as creatinine. In some cases, the tracer may include poly(ethylene) glycol, for example, PEG 300, PEG 400, PEG 2000, PEG 3350, or PEG 8000 (where "PEG" stands for poly(ethylene) glycol and the number indicates the molecular weight). Further examples of tracers are disclosed in International Patent Application No. PCT/US2010/000919, entitled "Determination of Tracers Within Subjects," filed on Mar. 26, 2010, incorporated herein by reference in its entirety.

In some cases, the device is a covert device, i.e., the device is formed into a something that does not appear to be a medical device. For example, the device may be embedded within a chair, a book, an umbrella, or a steering wheel, such that the device is able to inject a fluid or tracer into a subject without the subject ever being aware that the subject was exposed to the device. For example, by injecting a subject with a tracer, movements of the subject may be determined, for example, if the subject goes through an area they are not authorized to enter, or passes through an area of concern, such as a terrorist training camp or a military base.

In some embodiments, the device may be used to monitor a population of individuals. For example, the population may be a population entering a certain area (e.g., a border region, a town, a neighborhood, etc.), a population of subjects in a hospital, a medical facility, a nursing home, a school, or the like. Subjects having the tracer (knowingly or not) may be identified and distinguished from subjects not having the tracer, for example, as is discussed herein. Such data may be used, for example, for epidemiological purposes, to track the spread of diseases (such as contagious diseases, e.g., influenza or colds), to monitor the health of the population, to audit the performance of an institution (e.g., a hospital, a nursing home, a school), or the like. In some cases, such data may be used to set up quarantines, e.g., in the case of infectious diseases. In certain instances, such data may also be combined with additional data, for example, positional data from GPS systems or the like, as is discussed herein.

In certain embodiments, a fluid such as blood may be received from a population of individuals. For instance, devices including microneedles, or other devices such as those described herein, may be used to receive blood from patients (knowingly or otherwise), and then a condition of the subject determined, e.g., by determining an analyte within the blood (or other fluid). Examples of analytes determinable in a subject include, but are not limited to, glucose, tracers such as inulin, ions, or the like. Accordingly, characteristics of the population of individuals may be determined by determining the analyte in certain embodiments.

In some aspects, the device may be sold together with the drug or other pharmaceutical, e.g., as part of a kit. For example, the kit may include a drug or other pharmaceutical, and a device able to determine a species within the skin of a subject, e.g., a species indicative of the drug or other pharmaceutical, as previously discussed. In other embodiments, however, the device may be sold separately from the drug or other pharmaceutical. For example, a doctor or other medical personnel may prescribe a drug (or other pharmaceutical) to a subject, and optionally, the doctor or other medical personnel may prescribe a device of the invention, either separately, or together (e.g., as in a kit). In some cases, however, the device itself may be readily available to the subject, e.g., obtainable over-the-counter (OTC) or without a prescription. It should be noted that even if the drug itself requires a prescription, if the device is sold separately (without the drug), it need not necessarily also require a prescription to be purchased. Further examples of kits are discussed in detail below.

As previously discussed, in some embodiments, the device is able to deliver and/or receive fluid from the skin of a subject, or other mucosal surface, as well as methods of use thereof. In some cases, the device may pierce the skin of the subject, and fluid can then be delivered and/or received from the subject. The subject is usually human, although non-human subjects may be used in certain instances, for instance, other mammals such as a dog, a cat, a horse, a rabbit, a cow, a pig, a sheep, a goat, a rat (e.g., *Rattus Norvegicus*), a mouse (e.g., *Mus musculus*), a guinea pig, a hamster, a primate (e.g., a monkey, a chimpanzee, a baboon, an ape, a gorilla, etc.), or the like. If a fluid is received from the subject, the fluid may be any suitable bodily fluid. In certain embodiments, essentially any body fluid can be used, such as interstitial fluid, other skin-associated material, mucosal material or fluid, whole blood, perspiration and saliva, plasma, or any other bodily fluid.

Non-limiting examples of various devices of the invention are shown in FIG. 1. In FIG. 1A, device 90 is used for receiving a fluid from a subject when the device is placed on the skin of a subject. Device 90 includes sensor 95 and substance transfer component 92, e.g., including a needle, a microneedle, etc., as discussed herein. In fluidic communication with substance transfer component 92 via fluidic channel 99 is sensing chamber 97. In one embodiment, sensing chamber 97 may contain agents such as particles, enzymes, dyes, etc., for analyzing bodily fluids, such as interstitial fluid or blood. In some cases, fluid may be received using substance transfer component 92 by a vacuum, for example, a self-contained vacuum contained within device 90. Optionally, device 90 also contains a display 94 and associated electronics 93, batteries or other power supplies, etc., which may be used to display sensor readings obtained via sensor 95. In addition, device 90 may also optionally contain memory 98, transmitters for transmitting a signal indicative of sensor 95 to a receiver, etc.

In the example shown in FIG. 1A, device 90 may contain a vacuum source (not shown) that is self-contained within device 90, although in other embodiments, the vacuum source may be external to device 90. (In still other instances, other systems may be used to deliver and/or receive fluid from the skin, as is discussed herein.) In one embodiment, after being placed on the skin of a subject, the skin may be drawn upward into a recess of the substance transfer component 92, for example, upon exposure to the vacuum source. Access to the vacuum source may be controlled by any suitable method, e.g., by piercing a seal or a septum; by opening a valve or moving a gate, etc. For instance, upon activation of device 90, e.g., by the subject, remotely, automatically, etc., the vacuum source may be put into fluidic communication with the recess such that skin is drawn into the recess due to the vacuum. Skin drawn into the recess may come into contact with a skin insertion object (e.g., solid or hollow needles), which may, in some cases, pierce the skin and allow a fluid to be delivered and/or received from the skin. In another embodiment, a skin insertion object may be actuated and moved downward to come into contact with the skin, and optionally retracted after use, e.g., with deployment actuator 999. Device 90 also contains drug reservoir 995.

Figure 1B:
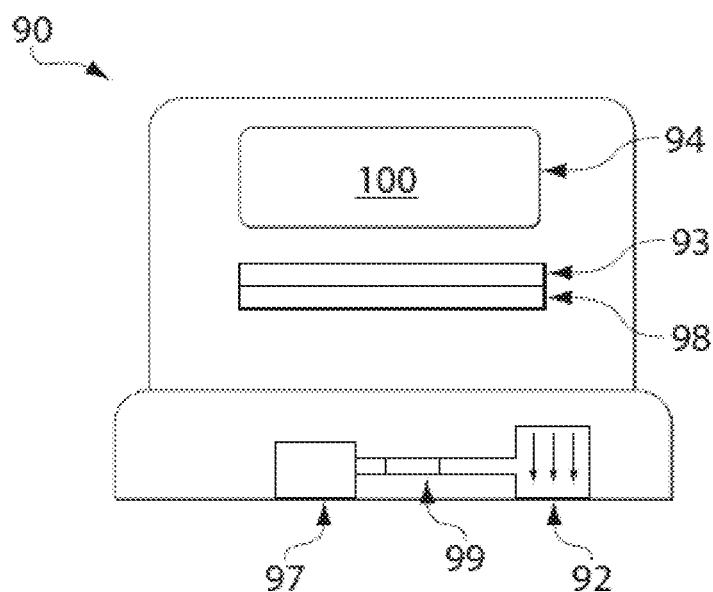

Another non-limiting example of a device is shown in FIG. 1B. This figure illustrates a device useful for delivering a fluid to the subject. Device 90 in this figure includes substance transfer component 92, e.g., including a needle, a microneedle, etc., as discussed herein. In fluidic communication with substance transfer component 92 via fluidic channel 99 is chamber 97, which may contain a drug or other agent to be delivered to the subject. In some cases, fluid may be delivered with a pressure controller, and/or received using substance transfer component 92 by a vacuum, for example, a self-contained vacuum contained within device 90. For instance, upon creating a vacuum, skin may be drawn up towards substance transfer component 92, and the substance transfer component 92 may pierce the skin. Fluid from chamber 97 can then be delivered into the skin through fluid channel 99 and substance transfer component 92. Optionally, device 90 also contains a display 94 and associated electronics 93, batteries or other power supplies, etc., which may be used control delivery of fluid to the skin. In addition, device 90 may also optionally contain memory 98, transmitters for transmitting a signal indicative of device 90 or fluid delivery to a receiver, etc.

Figure 2A:
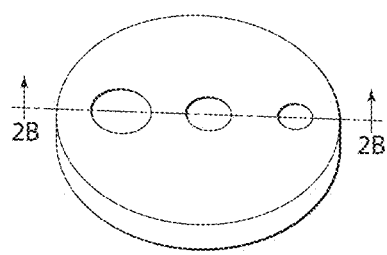
FIGS. 2A-2C illustrate devices according to various embodiments of the invention.
Figure 2B:
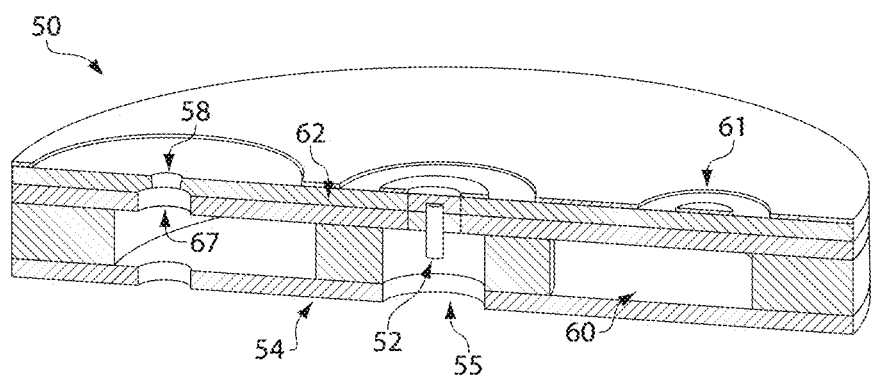

Yet another non-limiting example of a device of the invention is shown in FIG. 2. FIG. 2A illustrates a view of the device (with the cover removed), while FIG. 2B schematically illustrates the device in cross-section. In FIG. 2B, device 50 includes a needle 52 contained within a recess 55. Needle 52 may be solid or hollow, depending on the embodiment. Device 50 also includes a self-contained vacuum chamber 60, which wraps around the central portion of the device where needle 52 and recess 55 are located. A channel 62 connects vacuum chamber 60 with recess 55, separated by a foil or a membrane 67. Also shown in device 50 is button 58. When pushed, button 58 breaks foil 67, thereby connecting vacuum chamber 50 with recess 55, creating a vacuum in recess 55. The vacuum may be used, for example, to draw skin into recess 55, preferably such that it contacts needle 52 and pierces the surface, thereby gaining access to an internal fluid. The fluid may be controlled, for example, by controlling the size of needle 52, and thereby the depth of penetration. For example, the penetration may be limited to the epidermis, e.g., to collect interstitial fluid, or to the dermis, e.g., to collect blood. In some cases, the vacuum may also be used to at least partially secure device 50 on the surface of the skin, and/or to assist in the receiving of fluid from the skin. For instance, fluid may flow into channel 62 under action of the vacuum, and optionally to sensor 61, e.g., for detection of an analyte contained within the fluid. For instance, sensor 61 may produce a color change if an analyte is present, or otherwise produce a detectable signal.

Other components may be added to the example of the device illustrated in FIG. 2, in some embodiments of the invention. For example, device 50 may contain a cover, displays, ports, transmitters, sensors, channels such as microfluidic channels, chambers, and/or various electronics, e.g., to control or monitor fluid transport into or out of device 50, to determine an analyte present within a fluid delivered and/or received from the skin, to determine the status of the device, to report or transmit information regarding the device and/or analytes, or the like, as is discussed in more detail herein. As another example, device 50 may contain an adhesive, e.g., on surface 54, for adhesion of the device to the skin.

Figure 2C:
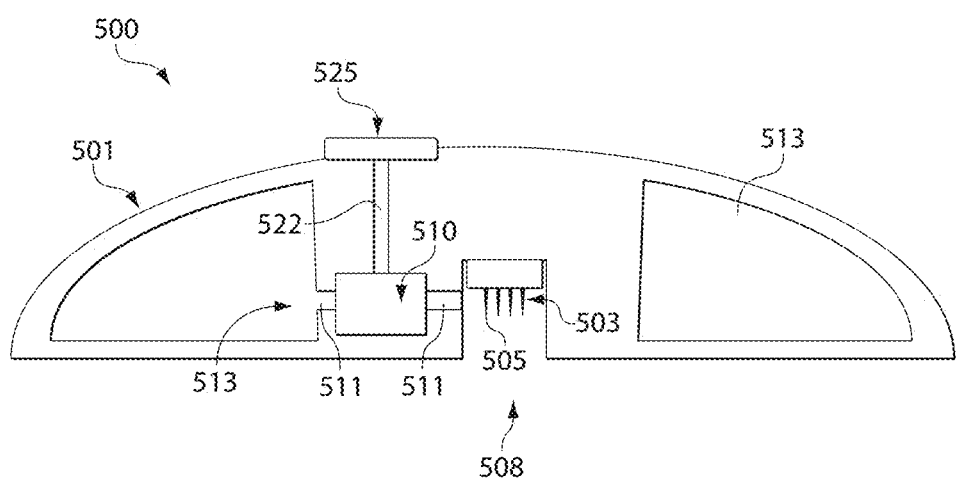

Yet another non-limiting example is illustrated with reference to FIG. 2C. In this example, device 500 includes a housing 501, and an associated substance transfer component 503. Substance transfer component 503 includes a plurality of needles or microneedles 505, although other skin insertion objects or flow activators as discussed herein may also be used. Also shown in FIG. 2C is sensor 510, connected via channels 511 to recess 508 containing needles or microneedles 505. Chamber 513 may be a self-contained vacuum chamber, and chamber 513 may be in fluidic communication with recess 508 via channel 511, for example, as controlled by a controller or an actuator (not shown). In this figure, device 500 also contains display 525, which is connected to sensor 510 via electrical connection 522. As an example of use of device 500, when fluid is drawn from the skin (e.g., blood, interstitial fluid, etc.), the fluid may flow through channel 511 to be determined by sensor 510, e.g., due to action of the vacuum from vacuum chamber 513. In some cases, the vacuum is used, for example, to draw skin into recess 508, preferably such that it contacts needles or microneedles 505 and pierces the surface of the skin to gain access to a fluid internal of the subject, such as blood or interstitial fluid, etc. The fluid may be controlled, for example, by controlling the size of needle 505, and thereby the depth of penetration. For example, the penetration may be limited to the epidermis, e.g., to collect interstitial fluid, or to the dermis, e.g., to collect blood. Upon determination of the fluid and/or an analyte present or suspected to be present within the fluid, a microprocessor or other controller may display on display 525 a suitable signal. As is discussed below, a display is shown in this figure by way of example only; in other embodiments, no display may be present, or other signals may be used, for example, lights, smell, sound, feel, taste, or the like.

In some cases, more than one substance transfer component may be present within the device. For instance, the device may be able to be used repeatedly, and/or the device may be able to deliver and/or receive fluid at more than one location on a subject, e.g., sequentially and/or simultaneously. In some cases, the device may be able to simultaneously deliver and receive fluid to and from a subject. A non-limiting example of a device having more than one substance transfer component is illustrated with reference to FIG. 2E. In this example, device 500 contains a plurality of structures such as those described herein for delivering and/or receiving fluid from a subject. For example, device 500 in this example contains 3 such units, although any number of units are possible in other embodiments. In this example, device 500 contains three such substance transfer components 575. Each of these substance transfer components may independently have the same or different structures, depending on the particular application, and they may have structures such as those described herein.

In some embodiments, the device may be an electrical and/or a mechanical device applicable or affixable to the surface of the skin, e.g., using adhesive, or other techniques such as those described herein. The adhesive may be permanent or temporary, and may be used to affix the device to the surface of the skin. The adhesive may be any suitable adhesive, for example, a pressure sensitive adhesive, a contact adhesive, a permanent adhesive, a hydrogel, a cyanoacrylate, a glue, a gum, hot melts, an epoxy, or the like. In some cases, the adhesive is chosen to be biocompatible or hypoallergenic.

As another example, the device may be a handheld device that is applied to the surface of the skin of a subject. In some cases, however, the device may be sufficiently small or portable that the subject can self-administer the device. In certain embodiments, the device may also be powered. In some instances, the device may be applied to the surface of the skin, and is not inserted into the skin. In other embodiments, however, at least a portion of the device may be inserted into the skin, for example, mechanically. For example, in one embodiment, the device may include a cutter, such as a hypodermic needle, a knife blade, a piercing element (e.g., a solid or hollow needle), or the like, as discussed herein.

In some cases, the device may be designed such that portions of the device are separable. For example, a first portion of the device may be removed from the surface of the skin, leaving other portions of the device behind on the skin. In one embodiment, a stop may also be included to prevent or control the depth to which the cutter or other device inserts into the skin, e.g., to control penetration to the epidermis, dermis, etc.

Any or all of the arrangements described herein can be provided proximate a subject, for example on or proximate a subject's skin. Activation of the devices can be carried out as described herein. For example, an on-skin device can be in the form of a patch or the like, optionally including multiple layers for activation, sensing, fluid flow, etc. Activation of the devices can be carried out in a variety of ways. In one manner, a patch can be applied to a subject and a region of the patch activated (e.g., tapped by a user) to inject a microneedle so as to access interstitial fluid. The same or a different tapping or pushing action can activate a vacuum source, open and/or close one or more of a variety of valves, or the like. The device can be a simple one in which it is applied to the skin and operates automatically (where e.g., application to the skin access interstitial fluid and draws interstitial fluid into an analysis region) or the patch or other device can be applied to the skin and one tapping or other activation can cause fluid to flow through administration of a microneedle, opening of a valve, activation of vacuum, or any combination. Any number of activation protocols can be carried out by a user repeatedly pushing or tapping a location or selectively, sequentially, and/or periodically activating a variety of switches (e.g., tapping regions of a patch). With this description, those of ordinary skill in the art can understand how any of the assays described above with respect to one and two can be facilitated. In another arrangement, activation of microneedles, creation of suction blisters, opening and/or closing of valves, and other techniques to facilitate one or more analysis can be carried out electronically or in other manners facilitated by the subject or by an outside controlling entity. For example, a device or patch can be provided proximate a subject's skin and a radio frequency, electromagnetic, or other signal can be provided by a nearby controller or a distant source to activate any of the needles, blister devices, valves or other components of the devices described so that any assay or assays can be carried out as desired.

As discussed, various devices of the invention include various systems and methods for delivering and/or receiving fluid from the subject, according to certain embodiments. For instance, the device may comprise a hypodermic needle, a vacuum source, a hygroscopic agent, or the like. Non-limiting examples of suitable delivery techniques include, but are not limited to, injection (e.g., using needles such as hypodermic needles) or a jet injector, such as those discussed below. For instance, in one embodiment, the fluid is delivered and/or received manually, e.g., by manipulating a plunger on a syringe. In another embodiment, the fluid can be delivered and/or received from the skin mechanically or automatically, e.g., using a piston pump or the like. Fluid may also be received using vacuums such as those discussed herein. For example, vacuum may be applied to a conduit, such as a needle, in fluidic communication with interstitial fluid. In yet another embodiment, fluid is received using capillary action (e.g., using a hypodermic needle having a suitably narrow inner diameter). In still another embodiment, pressure may be applied to force fluid out of the needle.

For instance, fluids received from the subject will often contain various analytes within the body that are important for diagnostic purposes, for example, markers for various disease states, such as glucose (e.g., for diabetics); other example analytes include ions such as sodium, potassium, chloride, calcium, magnesium, and/or bicarbonate (e.g., to determine dehydration); gases such as carbon dioxide or oxygen; $H^+$ (i.e., pH); metabolites such as urea, blood urea nitrogen or creatinine; hormones such as estradiol, estrone, progesterone, progestin, testosterone, androstenedione, etc. (e.g., to determine pregnancy, illicit drug use, or the like); or cholesterol. Other examples include insulin, or hormone levels. As discussed herein, certain embodiments of the present invention are generally directed at methods for receiving fluids from the body, and optionally determining one or more analytes within the received fluid. Thus, in some embodiments, at least a portion of the fluid may be stored, and/or analyzed to determine one or more analytes, e.g., a marker for a disease state, or the like. The fluid received from the skin may be subjected to such uses, and/or one or more materials previously delivered to the skin may be subject to such uses.

In other embodiments, fluid may be delivered to the subject, and such fluids may contain materials useful for delivery, e.g., forming at least a portion of the fluid, dissolved within the fluid, carried by the fluid (e.g., suspended or dispersed), or the like. Examples of suitable materials include, but are not limited to, particles such as microparticles or nanoparticles, a chemical, a drug or a therapeutic agent, a diagnostic agent, a carrier, or the like.

As used herein, the term "fluid" generally refers to a substance that tends to flow and to conform to the outline of its container. Typically, fluids are materials that are unable to withstand a static shear stress, and when a shear stress is applied, the fluid experiences a continuing and permanent distortion. The fluid may have any suitable viscosity that permits at least some flow of the fluid. Non-limiting examples of fluids include liquids and gases, but may also include free-flowing solid particles, viscoelastic fluids, and the like. For example, the fluid may include a flowable matrix or a gel, e.g., formed from biodegradable and/or biocompatible material such as polylactic acid, polyglycolic acid, poly(lactic-co-glycolic acid), etc., or other similar materials.

In other cases, however, the materials delivered to the subject may be used to determine conditions that are external to the subject. For example, the materials may contain reaction entities able to recognize pathogens or other environmental conditions surrounding the subject, for example, an antibody able to recognize an external pathogen (or pathogen marker). As a specific example, the pathogen may be anthrax and the antibody may be an antibody to anthrax spores. As another example, the pathogen may be a *Plasmodia* (some species of which causes malaria) and the antibody may be an antibody that recognizes the *Plasmodia*.

According to one set of embodiments, many devices as discussed herein use various techniques for delivering and/or receiving fluid, for example, in connection with substance transfer components, skin insertion objects, or the like. For example, one or more needles and/or microneedles, a hygroscopic agent, a cutter or other piercing element, an electrically-assisted system, or the like may be used in conjunction with a snap dome or other device as described above. Additional examples of such techniques are described herein and/or in the applications incorporated herein. It is to be understood that, generally, fluids may be delivered and/or received in a variety of ways, and various systems and methods for delivering and/or receiving fluid from the skin (or other organs) are discussed below and/or in the applications incorporated herein. In some embodiments, for example, techniques for piercing or altering the surface of the skin to transport a fluid are discussed, for example, using a needle such as a hypodermic needle or microneedles, chemicals applied to the skin (e.g., penetration enhancers), jet injectors or other techniques such as those discussed below, etc.

As an example, in one embodiment, a needle such as a hypodermic needle can be used to deliver and/or receive fluid to or from the skin or other organ. Hypodermic needles are well-known to those of ordinary skill in the art, and can be obtained commercially with a range of needle gauges. For example, the needle may be in the 20-30 gauge range, or the needle may be 32 gauge, 33 gauge, 34 gauge, etc.

As an example, microneedles such as those disclosed in U.S. Pat. No. 6,334,856, issued Jan. 1, 2002, entitled "Microneedle Devices and Methods of Manufacture and Use Thereof," by Allen, et al., may be used to deliver and/or receive fluids or other materials to or from a subject. The microneedles may be hollow or solid, and may be formed from any suitable material, e.g., metals, ceramics, semiconductors, organics, polymers, and/or composites. Examples include, but are not limited to, pharmaceutical grade stainless steel, gold, titanium, nickel, iron, gold, tin, chromium, copper, alloys of these or other metals, silicon, silicon dioxide, and polymers, including polymers of hydroxy acids such as lactic acid and glycolic acid polylactide, polyglycolide, polylactide-co-glycolide, and copolymers with polyethylene glycol, polyanhydrides, polyorthoesters, polyurethanes, polybutyric acid, polyvaleric acid, polylactide-co-caprolactone, polycarbonate, polymethacrylic acid, polyethylenevinyl acetate, polytetrafluorethylene, or polyesters.

In some cases, more than one microneedle may be used. For example, arrays of microneedles may be used, and the microneedles may be arranged in the array in any suitable configuration, e.g., periodic, random, etc. In some cases, the array may have 3 or more, 4 or more, 5 or more, 6 or more, 10 or more, 15 or more, 20 or more, 35 or more, 50 or more, 100 or more, or any other suitable number of microneedles. In some embodiments, the device may have at least 3 but no more than 5 needles or microneedles (or other skin insertion objects), at least 6 but no more than 10 needles or microneedles, or at least 11 but no more than 20 needles or microneedles. Typically, a microneedle will have an average cross-sectional dimension (e.g., diameter) of less than about a micron. It should be understood that references to "needle" or "microneedle" as discussed herein are by way of example and ease of presentation only, and that in other embodiments, more than one needle and/or microneedle may be present in any of the descriptions herein.

As still another example, pressurized fluids may be used to deliver fluids or other materials into the skin, for instance, using a jet injector or a "hypospray." Typically, such devices produce a high-pressure "jet" of liquid or powder (e.g., a biocompatible liquid, such as saline) that drives material into the skin, and the depth of penetration may be controlled, for instance, by controlling the pressure of the jet. The pressure may come from any suitable source, e.g., a standard gas cylinder or a gas cartridge. A non-limiting example of such a device can be seen in U.S. Pat. No. 4,103,684, issued Aug. 1, 1978, entitled "Hydraulically Powered Hypodermic Injector with Adapters for Reducing and Increasing Fluid Injection Force," by Ismach. Pressurization of the liquid may be achieved, for example, using compressed air or gas, for instance, from a gas cylinder or a gas cartridge.

In some embodiments, fluid may be received using a hygroscopic agent applied to the surface of the skin, or proximate the skin. For example, a device as described herein may contain a hygroscopic agent. In some cases, pressure may be applied to drive the hygroscopic agent into the skin. Hygroscopic agents typically are able to attract water from the surrounding environment, for instance, through absorption or adsorption. Non-limiting examples of hygroscopic agents include sugar, honey, glycerol, ethanol, methanol, sulfuric acid, methamphetamine, iodine, many chloride and hydroxide salts, and a variety of other substances. Other examples include, but are not limited to, zinc chloride, calcium chloride, potassium hydroxide, or sodium hydroxide. In some cases, a suitable hygroscopic agent may be chosen based on its physical or reactive properties, e.g., inertness or biocompatibility towards the skin of the subject, depending on the application.

In some embodiments, the device may comprise a cutter able to cut or pierce the surface of the skin. The cutter may comprise any mechanism able to create a path through which fluids may be delivered and/or received from the skin. For example, the cutter may comprise a hypodermic needle, a blade (e.g., a knife blade, a serrated blade, etc.), a piercing element (e.g., a lancet or a solid or a hollow needle), or the like, which can be applied to the skin to create a suitable conduit for the delivery and/or receiving of fluid from the skin. In one embodiment, a cutter is used to create such a pathway and removed, then fluid may be delivered and/or received via this pathway. In another embodiment, the cutter remains in place within the skin, and fluid may be delivered and/or received through a conduit within the cutter.

In some embodiments, fluid may be received using an electric charge. For example, reverse iontophoresis may be used. Without wishing to be bound by any theory, reverse iontophoresis uses a small electric current to drive charged and highly polar compounds across the skin. Since the skin is negatively charged at physiologic pH, it acts as a permselective membrane to cations, and the passage of counterions across the skin induces an electroosmotic solvent flow that may carry neutral molecules in the anode-to-cathode direction. Components in the solvent flow may be analyzed as described elsewhere herein. In some instances, a reverse iontophoresis apparatus may comprise an anode cell and a cathode cell, each in contact with the skin. The anode cell may be filled, for example, with an aqueous buffer solution (i.e., aqueous Tris buffer) having a pH greater than 4 and an electrolyte (i.e. sodium chloride). The cathode cell can be filled with aqueous buffer. As one example, a first electrode (e.g., an anode) can be inserted into the anode cell and a second electrode (e.g., a cathode) can be inserted in the cathode cell. In some embodiments, the electrodes are not in direct contact with the skin.

A current may be applied to induce reverse iontophoresis, thereby receiving a fluid from the skin. The current applied may be, for example, greater than 0.01 mA, greater than 0.3 mA, greater than 0.1 mA, greater than 0.3 mA, greater than 0.5 mA, or greater than 1 mA. It should be understood that currents outside these ranges may be used as well. The current may be applied for a set period of time. For example, the current may be applied for greater than 30 seconds, greater than 1 minute, greater than 5 minutes, greater than 30 minutes, greater than 1 hour, greater than 2 hours, or greater than 5 hours. It should be understood that times outside these ranges may be used as well.

In one set of embodiments, the device may comprise a substance transfer component in the form of an apparatus for ablating the skin. Without wishing to be bound by any theory, it is believed that ablation comprises removing a microscopic patch of stratum corneum (i.e., ablation forms a micropore), thus allowing access to bodily fluids. In some cases, thermal, radiofrequency, and/or laser energy may be used for ablation. In some instances, thermal ablation may be applied using a heating element. Radiofrequency ablation may be carried out using a frequency and energy capable of heating water and/or tissue. A laser may also be used to irradiate a location on the skin to remove a portion. In some embodiments, the heat may be applied in pulses such that a steep temperature gradient exists essentially perpendicular to the surface of the skin. For example, a temperature of at least 100° C., at least 200° C., at least 300° C., or at least 400° C. may be applied for less than 1 second, less than 0.1 seconds, less than 0.01 seconds, less than 0.005 seconds, or less than 0.001 seconds.

In some embodiments, the device may comprise a substance transfer component in the form of a mechanism for taking a solid sample of tissue. For example, a solid tissue sample may be acquired by methods such as scraping the skin or cutting out a portion. Scraping may comprise a reciprocating action whereby an instrument is scraped along the surface of the skin in two or more directions. Scraping can also be accomplished by a rotating action, for example parallel to the surface of the skin and in one direction (i.e., with a roller drum) or parallel to the surface of the skin and in a circular manner (i.e., with a drilling instrument). A cutting mechanism may comprise a blade capable of making one or more incisions and a mechanism for removing a portion of tissue (i.e., by suction or mechanically picking up) or may use a pincer mechanism for cutting out a portion of tissue. A cutting mechanism may also function by a coring action. For example, a hollow cylindrical device can be penetrated into the skin such that a cylindrical core of tissue may be removed. A solid sample may be analyzed directly or may be liquefied prior to analysis. Liquefaction can comprise treatment with organic solvents, enzymatic solutions, surfactants, etc.

In some embodiments, fluids may be delivered to or received from the skin using vacuum. The vacuum may be an external vacuum source, and/or the vacuum source may be self-contained within the device. For example, vacuums of at least about 50 mmHg, at least about 100 mmHg, at least about 150 mmHg, at least about 200 mmHg, at least about 250 mmHg, at least about 300 mmHg, at least about 350 mmHg, at least about 400 mmHg, at least about 450 mmHg, at least about 500 mmHg, at least 550 mmHg, at least 600 mmHg, at least 650 mmHg, at least about 700 mmHg, or at least about 750 mmHg may be applied to the skin. As used herein, "vacuum" refers to pressures that are below atmospheric pressure.

As mentioned, any source of vacuum may be used. For example, the device may comprise an internal vacuum source, and/or be connectable to a vacuum source is external to the device, such as a vacuum pump or an external (line) vacuum source. In some cases, vacuum may be created manually, e.g., by manipulating a syringe pump, a plunger, or the like, or the low pressure may be created mechanically or automatically, e.g., using a piston pump, a syringe, a bulb, a Venturi tube, manual (mouth) suction, etc., or the like.

In one set of embodiments, a device of the present invention may not have an external power and/or a vacuum source. In some cases, the device is "pre-loaded" with a suitable vacuum source; for instance, in one embodiment, the device may be applied to the skin and activated in some fashion to create and/or access the vacuum source. As one example, a device of the present invention may be contacted with the skin of a subject, and a vacuum created through a change in shape of a portion of the device (e.g., using a shape memory polymer), or the device may contain one or more sealed, self-contained vacuum chambers, where a seal is punctured in some manner to create a vacuum. For instance, upon puncturing the seal, a vacuum chamber may be in fluidic communication with a needle, which can be used to move the skin towards the device, receive fluid from the skin, or the like.

In some embodiments, the device may be an electrical and/or a mechanical device applicable or affixable to the surface of the skin, e.g., using adhesive, or other techniques such as those described herein. The adhesive may be permanent or temporary, and may be used to affix the device to the surface of the skin. The adhesive may be any suitable adhesive, for example, a pressure sensitive adhesive, a contact adhesive, a permanent adhesive, a hydrogel, a cyanoacrylate, a glue, a gum, hot melts, an epoxy, or the like. In some cases, the adhesive is chosen to be biocompatible or hypoallergenic.

In another set of embodiments, the device may be mechanically held to the skin, for example, the device may include mechanical elements such as straps, belts, buckles, strings, ties, elastic bands, or the like. For example, a strap may be worn around the device to hold the device in place against the skin of the subject. In yet another set of embodiments, a combination of these and/or other techniques may be used. As one non-limiting example, the device may be affixed to a subject's arm or leg using adhesive and a strap.

In some embodiments, the device may include a support structure for application to the skin of the subject. The support structure may be used, as discussed herein, for applying the substance transfer component to the surface of the skin of the subject, e.g., so that fluid may be delivered and/or received from the skin of the subject. In some cases, the support structure may immobilize the substance transfer component such that the substance transfer component cannot move relative to the support structure; in other cases, however, the substance transfer component may be able to move relative to the support structure. In one embodiment, as a non-limiting example, the substance transfer component is immobilized relative to the support structure, and the support structure is positioned within the device such that application of the device to the skin causes at least a portion of the substance transfer component to pierce the skin of the subject.

In some embodiments, the deployment actuator, or a portion of the deployment actuator, may move from a first position to a second position. For example, the first position may be one where the deployment actuator has attached thereto a substance transfer component that is not in contact with the skin (e.g., a skin insertion object of the substance transfer component may be contained within a recess of the substance transfer component), while the second position of the deployment actuator may be one where the substance transfer component does contact the skin, e.g., to pierce the skin. The deployment actuator may be moved using any suitable technique, e.g., manually, mechanically, electromagnetically, using a servo mechanism, or the like. In one set of embodiments, for example, the deployment actuator may be moved from a first position to a second position by pushing a button on the device, which causes the deployment actuator to move (either directly, or through a mechanism linking the button with the deployment actuator). Other mechanisms (e.g., dials, levers, sliders, etc., as discussed herein) may be used in conjunction of or instead of a button. In another set of embodiments, the deployment actuator may be moved from a first position to a second position automatically, for example, upon activation by a computer, upon remote activation, after a period of time has elapsed, or the like. For example, in one embodiment, a servo connected to the deployment actuator is activated electronically, moving the deployment actuator from the first position to the second position. In some cases, the deployment actuator may include a triggering mechanism that initiates deployment.

In some cases, the deployment actuator and/or the substance transfer component may also be moved from the second position to the first position (or some other position). For example, after fluid has been delivered and/or received from the skin, e.g., using a substance transfer component, the deployment actuator may be moved, which may move the substance transfer component away from contact with the skin. The deployment actuator may be moved from the second position to the first position using any suitable technique, including those described above, and the technique for moving the deployment actuator from the second position to the first position may be the same or different as that moving the deployment actuator from the first position to the second position.

In some cases, the device may be able to draw skin towards the substance transfer component. For example, in one set of embodiments, the device may include a vacuum interface or region. The interface or region may be connected with a vacuum source (external and/or internal to the device), and when a vacuum is applied, skin may be drawn towards the device, e.g., for contact with a substance transfer component, such as one or more needles or microneedles.

In certain embodiments, the may also include a device actuator. The device actuator may be constructed and arranged to cause exposure of the substance transfer component to the skin upon actuation of the device actuator. For example, the activator may cause the substance transfer component to release a chemical to contact the skin, a microneedle or other substance transfer component to be driven into the skin, a vacuum to be applied to the skin, a jet of fluid to be directed to the skin, or the like. The device actuator may be actuated by the subject, and/or by another person (e.g., a health care provider), or the device itself may be self-actuating, e.g., upon application to the skin of a subject. The actuator may be actuated once, or multiple times in some cases.

The device may be activated, for example, by pushing a button, pressing a switch, moving a slider, turning a dial, or the like. The subject, and/or another person, may activate the device activator. In some cases, the device may be remotely activated. For example, a health care provider may send an electromagnetic signal which is received by the device in order to activate the device, e.g., a wireless signal, a Bluetooth signal, an Internet signal, a radio signal, etc.

In one set of embodiments, the device may include channels such as microfluidic channels, which may be used to deliver and/or receive fluids and/or other materials into or out of the skin. In some cases, the microfluidic channels are in fluid communication with a substance transfer component that is used to deliver and/or receive fluids to or from the skin. For example, in one set of embodiments, the device may include a hypodermic needle that can be inserted into the skin, and fluid may be delivered into the skin via the needle and/or received from the skin via the needle. The device may also include one or more microfluidic channels to contain fluid for delivery to the needle, e.g., from a source of fluid, and/or to receive fluid from the skin, e.g., for delivery to an analytical chamber within the device, to a reservoir for later analysis, or the like.

In some cases, more than one chamber may be present within the device, and in some cases, some or all of the chambers may be in fluidic communication, e.g., via channels such as microfluidic channels. In various embodiments, a variety of chambers and/or channels may be present within the device, depending on the application. For example, the device may contain chambers for sensing an analyte, chambers for holding reagents, chambers for controlling temperature, chambers for controlling pH or other conditions, chambers for creating or buffering pressure or vacuum, chambers for controlling or dampening fluid flow, mixing chambers, or the like.

Thus, in one set of embodiments, the device may include a microfluidic channel. As used herein, "microfluidic," "microscopic," "microscale," the "micro-" prefix (for example, as in "microchannel"), and the like generally refers to elements or articles having widths or diameters of less than about 1 mm, and less than about 100 microns (micrometers) in some cases. In some embodiments, larger channels may be used instead of, or in conjunction with, microfluidic channels for any of the embodiments discussed herein. For example, channels having widths or diameters of less than about 10 mm, less than about 9 mm, less than about 8 mm, less than about 7 mm, less than about 6 mm, less than about 5 mm, less than about 4 mm, less than about 3 mm, or less than about 2 mm may be used in certain instances. In some cases, the element or article includes a channel through which a fluid can flow. In all embodiments, specified widths can be a smallest width (i.e. a width as specified where, at that location, the article can have a larger width in a different dimension), or a largest width (i.e. where, at that location, the article has a width that is no wider than as specified, but can have a length that is greater). Thus, for instance, the microfluidic channel may have an average cross-sectional dimension (e.g., perpendicular to the direction of flow of fluid in the microfluidic channel) of less than about 1 mm, less than about 500 microns, less than about 300 microns, or less than about 100 microns. In some cases, the microfluidic channel may have an average diameter of less than about 60 microns, less than about 50 microns, less than about 40 microns, less than about 30 microns, less than about 25 microns, less than about 10 microns, less than about 5 microns, less than about 3 microns, or less than about 1 micron.

A "channel," as used herein, means a feature on or in an article (e.g., a substrate) that at least partially directs the flow of a fluid. In some cases, the channel may be formed, at least in part, by a single component, e.g. an etched substrate or molded unit. The channel can have any cross-sectional shape, for example, circular, oval, triangular, irregular, square or rectangular (having any aspect ratio), or the like, and can be covered or uncovered (i.e., open to the external environment surrounding the channel). In embodiments where the channel is completely covered, at least one portion of the channel can have a cross-section that is completely enclosed, and/or the entire channel may be completely enclosed along its entire length with the exception of its inlet and outlet.

A channel may have any aspect ratio, e.g., an aspect ratio (length to average cross-sectional dimension) of at least about 2:1, more typically at least about 3:1, at least about 5:1, at least about 10:1, etc. As used herein, a "cross-sectional dimension," in reference to a fluidic or microfluidic channel, is measured in a direction generally perpendicular to fluid flow within the channel. A channel generally will include characteristics that facilitate control over fluid transport, e.g., structural characteristics and/or physical or chemical characteristics (hydrophobicity vs. hydrophilicity) and/or other characteristics that can exert a force (e.g., a containing force) on a fluid. The fluid within the channel may partially or completely fill the channel. In some cases the fluid may be held or confined within the channel or a portion of the channel in some fashion, for example, using surface tension (e.g., such that the fluid is held within the channel within a meniscus, such as a concave or convex meniscus). In an article or substrate, some (or all) of the channels may be of a particular size or less, for example, having a largest dimension perpendicular to fluid flow of less than about 5 mm, less than about 2 mm, less than about 1 mm, less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm or less in some cases. In one embodiment, the channel is a capillary.

A variety of materials and methods, according to certain aspects of the invention, can be used to form the device, e.g., microfluidic channels, chambers, etc. For example, various components of the invention can be formed from solid materials, in which the channels can be formed via micromachining, film deposition processes such as spin coating and chemical vapor deposition, laser fabrication, photolithographic techniques, etching methods including wet chemical or plasma processes, and the like. See, for example, *Scientific American,* 248:44-55, 1983 (Angell, et al).

In one set of embodiments, various components of the systems and devices of the invention can be formed of a polymer, for example, an elastomeric polymer such as polydimethylsiloxane ("PDMS"), polytetrafluoroethylene ("PTFE" or Teflon®), or the like. For instance, according to one embodiment, a microfluidic channel may be implemented by fabricating the fluidic system separately using PDMS or other soft lithography techniques (details of soft lithography techniques suitable for this embodiment are discussed in the references entitled "Soft Lithography," by Younan Xia and George M. Whitesides, published in the *Annual Review of Material Science,* 1998, Vol. 28, pages 153-184, and "Soft Lithography in Biology and Biochemistry," by George M. Whitesides, Emanuele Ostuni, Shuichi Takayama, Xingyu Jiang and Donald E. Ingber, published in the *Annual Review of Biomedical Engineering,* 2001, Vol. 3, pages 335-373; each of these references is incorporated herein by reference).

Other examples of potentially suitable polymers include, but are not limited to, polyethylene terephthalate (PET), polyacrylate, polymethacrylate, polycarbonate, polystyrene, polyethylene, polypropylene, polyvinylchloride, cyclic olefin copolymer (COC), polytetrafluoroethylene, a fluorinated polymer, a silicone such as polydimethylsiloxane, polyvinylidene chloride, bis-benzocyclobutene ("BCB"), a polyimide, a fluorinated derivative of a polyimide, or the like. Combinations, copolymers, or blends involving polymers including those described above are also envisioned. The device may also be formed from composite materials, for example, a composite of a polymer and a semiconductor material.

In some embodiments, various components of the invention are fabricated from polymeric and/or flexible and/or elastomeric materials, and can be conveniently formed of a hardenable fluid, facilitating fabrication via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, waxes, metals, or mixtures or composites thereof heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, etc.

Silicone polymers are used in certain embodiments, for example, the silicone elastomer polydimethylsiloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying fabrication of the microfluidic structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures of the invention from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, components can be fabricated and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in an article entitled "Rapid Prototyping of Microfluidic Systems and Polydimethylsiloxane," *Anal. Chem.*, 70:474-480, 1998 (Duffy et al.), incorporated herein by reference.

In some embodiments, the device may include a sensor, for example embedded within or integrally connected to the device, or positioned remotely but with physical, electrical, and/or optical connection with the device so as to be able to sense a compartment within the device. For example, the sensor may be in fluidic communication with fluid received from a subject, directly, via a microfluidic channel, an analytical chamber, etc. The sensor may be able to sense an analyte, e.g., one that is suspected of being in a fluid received from a subject. For example, a sensor may be free of any physical connection with the device, but may be positioned so as to detect the results of interaction of electromagnetic radiation, such as infrared, ultraviolet, or visible light, which has been directed toward a portion of the device, e.g., a chamber within the device. As another example, a sensor may be positioned on or within the device, and may sense activity in a chamber by being connected optically to the chamber. Sensing communication can also be provided where the chamber is in communication with a sensor fluidly, optically or visually, thermally, pneumatically, electronically, or the like, so as to be able to sense a condition of the chamber. As one example, the sensor may be positioned downstream of a chamber, within a channel such a microfluidic channel, on an external apparatus, or the like.

The sensor may be, for example, a pH sensor, an optical sensor, an oxygen sensor, a sensor able to detect the concentration of a substance, or the like. Non-limiting examples of sensors include dye-based detection systems, affinity-based detection systems, microfabricated gravimetric analyzers, CCD cameras, optical detectors, optical microscopy systems, electrical systems, thermocouples and thermistors, pressure sensors, etc. Those of ordinary skill in the art will be able to identify other suitable sensors. The sensor can include a colorimetric detection system in some cases, which may be external to the device, or microfabricated into the device in certain cases. As an example of a colorimetric detection system, if a dye or a fluorescent entity is used (e.g. in a particle), the colorimetric detection system may be able to detect a change or shift in the frequency and/or intensity of the dye or fluorescent entity.

Examples of analytes that the sensor may be used to determine include, but are not limited to, pH or metal ions, proteins, nucleic acids (e.g. DNA, RNA, etc.), drugs, sugars (e.g., glucose), hormones (e.g., estradiol, estrone, progesterone, progestin, testosterone, androstenedione, etc.), carbohydrates, or other analytes of interest. Other conditions that can be determined can include pH changes, which may indicate disease, yeast infection, periodontal disease at a mucosal surface, oxygen or carbon monoxide levels which indicate lung dysfunction, and drug levels, e.g., legal prescription levels of drugs such as coumadin, other drugs such as nicotine, or illegal such as cocaine. Further examples of analytes include those indicative of disease, such as cancer specific markers such as CEA and PSA, viral and bacterial antigens, and autoimmune indicators such as antibodies to double stranded DNA, indicative of Lupus. Still other conditions include exposure to elevated carbon monoxide, which could be from an external source or due to sleep apnea, too much heat (important in the case of babies whose internal temperature controls are not fully self-regulating) or from fever. Still other potentially suitable analytes include various pathogens such as bacteria or viruses, and/or markers produced by such pathogens.

As additional non-limiting examples, the sensor may contain an antibody able to interact with a marker for a disease state, an enzyme such as glucose oxidase or glucose 1-dehydrogenase able to detect glucose, or the like. The analyte may be determined quantitatively or qualitatively, and/or the presence or absence of the analyte within the received fluid may be determined in some cases. Those of ordinary skill in the art will be aware of many suitable commercially-available sensors, and the specific sensor used may depend on the particular analyte being sensed.

Still other potentially suitable analytes include various pathogens such as bacteria or viruses, and/or markers produced by such pathogens. Thus, in certain embodiments of the invention, as discussed below, one or more analytes within the pooled region of fluid may be determined in some fashion, which may be useful in determining a past, present and/or future condition of the subject.

In one embodiment as discussed below, an analyte may be determined as an "on/off" or "normal/abnormal" situation. Detection of the analyte, for example, may be indicative that insulin is needed; a trip to the doctor to check cholesterol; ovulation is occurring; kidney dialysis is needed; drug levels are present (e.g., especially in the case of illegal drugs) or too high/too low (e.g., important in care of geriatrics in particular in nursing homes). As another embodiment, however, an analyte may be determined quantitatively.

As described herein, any of a variety of signaling or display methods, associated with analyses, can be provided including signaling visually, by smell, sound, feel, taste, or the like, in some embodiments. Signal structures include, but are not limited to, displays (visual, LED, light, etc.), speakers, chemical-releasing compartments (e.g., containing a volatile chemical), mechanical devices, heaters, coolers, or the like. In some cases, the signal structure may be integral with the device (e.g., integrally connected with a support structure for application to the skin of the subject, e.g., containing a substance transfer component such as a microneedle), or the signal structure may not be integrally connected with the support structure.

In some embodiments, signaling methods such as these may be used to indicate the presence and/or concentration of an analyte determined by the sensor, e.g., to the subject, and/or to another entity, such as those described below. Where a visual signal is provided, it can be provided in the form of change in opaqueness, a change in intensity of color and/or opaqueness, or can be in the form of a message (e.g., numerical signal, or the like), an icon (e.g., signaling by shape or otherwise a particular medical condition), a brand, logo, or the like. For instance, in one embodiment, the device may include a display. A written message such as "take next dose," or "glucose level is high" or a numerical value might be provided, or a message such as "toxin is present." These messages, icons, logos, or the like can be provided as an electronic read-out by a component of a device and/or can be displayed in an inherent arrangement of one or more components of the device.

In some embodiments, a device is provided where the device determines a physical condition of a subject and produces a signal related to the condition that can be readily understood by the subject (e.g., by provision of a visual "OK" signal as described above) or can be designed so as not to be readily understandable by a subject. Where not readily understandable, the signal can take a variety of forms. In one form, the signal might be a series of letters or numbers that mean nothing to the subject (e.g., A1278CDQ) which would have meaning to a medical professional or the like (and/or be decodable by the same, e.g., with reference to a suitable decoder) and can be associated with a particular physiological condition. Alternatively, a signal in the form of bar code can be provided by a device such that, under a particular condition or set of conditions the bar code appears and/or disappears, or changes, and can be read by a bar code reader to communicate information about the subject or analyte. In another embodiment, the device can be designed such that an ultraviolet signal is produced, or a signal that can be read only under ultraviolet light (e.g., a simple spot or patch, or any other signal such as a series of number, letters, bar code, message, or the like that can be readily understandable or not readily understandable by a subject) can be provided. The signal may be invisible to the human eye but, upon application UV light or other excitation energy, may be readable. The signal can be easily readable or understandable by a user via visual observation, or with other sensory activity such smell, feel, etc. In certain embodiments, equipment as described above may be needed to determine a signal provided by the device, such as equipment in a clinical setting, etc. In some cases, the device is able to transmit a signal indicative of the analyte to a receiver, e.g., as a wireless signal, a Bluetooth signal, an Internet signal, a radio signal, etc.

In some embodiments, quantitative and/or qualitative analyses can be provided by a device. That is, the device in some cases may provide analyses that allow "yes/no" tests or the like, or tests that provide information on the quantity, concentration, or level of a particular analyte or analytes. Display configurations can be provided by the invention that reflect the amount of a particular analyte present in a subject at a particular point in time, or any other variable (presence of analysis over time, type of analyte, etc.) display configurations can take a variety of forms. In one example, a dial can be provided, similar to that of a speedometer with a series of level indications (e.g., numbers around the dial) and a "needle" or other device that indicates a particular level. In other configurations, a particular area of the device (e.g., on a display) can exist that is filled in to a greater or lesser extent depending upon the presence and/or quantity of a particular analyte present, e.g., in the form of a bar graph. In another arrangement a "color wheel" can be provided where the amount of a particular analyte present can control which colors of the wheel are visible. Or, different analytes can cause different colors of a wheel or different bars of a graph to become visible or invisible in a multiple analyte analysis. Multiple-analyte quantitative analyses can be reflected in multiple color wheels, a single color wheel with different colors per analyte where the intensity of each color reflects the amount of the analyte, or, for example, a plurality of bar graphs where each bar graph is reflective of a particular analyte and the level of the bar (and/or degree to which an area is filled in with visible color or other visible feature) is reflective of the amount of the analyte. As with all embodiments here, whatever signal is displayed can be understandable or not understandable to any number of participants. For example, it can be understandable to a subject or not understandable to a subject. Where not understandable it might need to be decoded, read electronically, or the like. Where read electronically, for example, a device may provide a signal that is not understandable to a subject or not even visible or otherwise able to be sensed by a subject, and a reader can be provided adjacent or approximate the device that can provide a visible signal that is understandable or not understandable to the subject, or can transmit a signal to another entity for analysis.

In connection with any signals associated with any analyses described herein, another, potentially related signal or other display (or smell, taste, or the like) can be provided which can assist in interpreting and/or evaluating the signal. In one arrangement, a calibration or control is provided proximate (or otherwise easily comparable with) a signal, e.g., a visual calibration/control or comparator next to or close to a visual signal provided by a device and/or implanted agents, particles, or the like.

A visual control or reference can be used with another sensory signal, such as that of smell, taste, temperature, itch, etc. A reference/control and/or experimental confirmation component can be provided, to be used in connection with an in-skin test or vice versa. References/indicators can also be used to indicate the state of life of a device, changing color or intensity and/or changing in another signaling aspect as the device changes relative to its useful life, so that a user can determine when the device should no longer be relied upon and/or removed. For certain devices, an indicator or control can be affected by adding analyte to the control (e.g., from a source outside of the source to be determine) to confirm operability of the device and/or to provide a reference against which to measure a signal of the device. For example, a device can include a button to be tapped by a user which will allow an analyte from a reservoir to transfer to an indicator region to provide a signal, to demonstrate operability of the device and/or provide a comparator for analysis.

Many of the embodiments described herein involve a quantitative analysis and related signal, i.e., the ability to determine the relative amount or concentration of an analyte in a medium. This can be accomplished in a variety of ways. For example, where an agent (e.g. a binding partner attached to a nanoparticle) is used to capture and analyze an analyte, the agent can be provided in a gradient in concentration across a sensing region of the device. Or a sensing region can include a membrane or other apparatus through which analyte is required to flow or pass prior to capture and identification, and the pathway for analyte travel can vary as a function of position of display region. For example, a membrane can be provided across a sensing region, through which analyte must pass prior to interacting with a layer of binding and/or signaling agent, and the membrane may vary in thickness laterally in a direction related to "bar graph" readout. Where a small amount of analyte is present, it may pass through the thinner portion but not the thicker portion of the membrane, but where a larger amount is present, it may pass across a thicker portion. The boundary (where one exists) between a region through which analyte passes, and one through which it does not completely pass, can define the "line" of the bar graph. Other ways of achieving the same or a similar result can include varying the concentration of a scavenger or transporter of the analyte, or an intermediate reactive species (between analyte and signaling event), across a membrane or other article, gradient in porosity or selectivity of the membrane, ability to absorb or transport sample fluid, or the like. These principles, in combination with other disclosure herein, can be used to facilitate any or all of the quantitative analyses described herein.

In certain embodiments, a subject having a condition such as a physiological condition to be analyzed (or other user, such as medical personnel) reads and/or otherwise determines a signal from a device. For example, the device may transmit a signal indicative of a condition of the subject and/or the device. Alternatively, or in addition, a signal produced by a device can be acquired in the form of a representation (e.g. a digitized signal, or the like) and transmitted to another entity for analysis and/or action. For example, a signal can be produced by a device, e.g., based on a sensor reading of an analyte, based on fluid delivered and/or received from the skin, based on a condition of the device, or the like. The signal may represent any suitable data or image. For example, the signal may represent the presence and/or concentration of an analyte in fluid received from a subject, the amount of fluid received from a subject and/or delivered to the subject, the number of times the device has been used, the battery life of the device, the amount of vacuum left in the device, the cleanliness or sterility of the device, the identity of the device (e.g., where multiple devices are given unique identification numbers, to prevent counterfeiting, accidental exchange of equipment to incorrect users, etc.), or the like. For instance, in some embodiments, an image of the signal (e.g., a visual image or photograph) can be obtained and transmitted to a different entity (for example, a user can take a cell phone picture of a signal generated by the device and send it, via cell phone, the other entity).

The other entity that the signal is transmitted to can be a human (e.g., a clinician) or a machine. In some cases, the other entity may be able to analyze the signal and take appropriate action. In one arrangement, the other entity is a machine or processor that analyzes the signal and optionally sends a signal back to the device to give direction as to activity (e.g., a cell phone can be used to transmit an image of a signal to a processor which, under one set of conditions, transmits a signal back to the same cell phone giving direction to the user, or takes other action). Other actions can include automatic stimulation of the device or a related device to dispense a medicament or pharmaceutical, or the like. The signal to direct dispensing of a pharmaceutical can take place via the same used to transmit the signal to the entity (e.g., cell phone) or a different vehicle or pathway. Telephone transmission lines, wireless networks, Internet communication, and the like can also facilitate communication of this type.

As one specific example, a device may be a glucose monitor. As signal may be generated by the device and an image of the signal captured by a cell phone camera and then transmitted via cell phone to a clinician. The clinician may then determine that the glucose (or e.g., insulin) level is appropriate or inappropriate and send a message indicating this back to the subject via cell phone.

Information regarding the analysis can also be transmitted to the same or a different entity, or a different location simply by removing the device or a portion of the device from the subject and transferring it to a different location. For example, a device can be used in connection with a subject to analyze presence and/or amount of a particular analyte. At some point after the onset of use, the device, or a portion of the device carrying a signal or signals indicative of the analysis or analyses, can be removed and, e.g., attached to a record associated with the subject. As a specific example, a patch can be worn by a subject to determine presence and/or amount of one or more analytes qualitatively, quantitatively, and/or over time. The subject can visit a clinician who can remove the patch or a portion of the patch and attach it to a medical record associated with the subject.

According to various sets of embodiments, the device may be used one, or multiple times, depending on the application. For instance, obtaining samples for sensing, according to certain embodiments of the invention, can be done such that sensing can be carried out continuously, discretely, or a combination of these. For example, where a bodily fluid such as interstitial fluid is accessed for determination of an analyte, fluid can be accessed discretely (i.e., as a single dose, once or multiple times), or continuously by creating a continuous flow of fluid which can be analyzed once or any number of times. Additionally, testing can be carried out once, at a single point in time, or at multiple points in time, and/or from multiple samples (e.g., at multiple locations relative to the subject).

Alternatively or in addition, testing can be carried out continuously over any number of points in time involving one or any number of locations relative to the subject or other multiple samples. As an example, one bolus or isolated sample, of fluid such as interstitial fluid can be obtained. From that fluid a test can be carried out to determine whether a particular analyte or other agent exists in the fluid. Alternatively, two or more tests can be carried out involving that quantity of fluid to determine the presence and/or quantity of two or more analytes, and any number of such tests can be carried out. Tests involving that quantity of fluid can be carried out simultaneously or over a period of time. For example, a test for a particular analyte can be carried out at various points in time to determine whether the result changes over time, or different analytes can be determined at different points in time. As another example, a pool of fluid can be formed between layers of skin via, e.g., a suction blister and either within the suction blister or from fluid drawn from the suction blister and placed elsewhere, any of the above and other analysis can be carried out at one or more points in time. Where a suction blister is formed in such a way that interstitial fluid within the blister changes over time (where an equilibrium exists between interstitial fluid within the subject and interstitial fluid in the suction blister itself, i.e., the fluid within the blister is ever changing to reflect the content of the interstitial fluid of the subject in the region of the blister over time). Testing of fluid within or from the suction blister at various points in time can provide useful information.

In another example, a microneedle or microneedles, or other device(s) can be used to access a fluid of a subject such as interstitial fluid or blood. Fluid can be drawn to a point of analysis and analyzed in any manner described herein. For example, an analysis can be carried out once, to determine the presence and/or quantity of a single analyte, or a number of tests can be carried out. From a single sample of fluid, a particular test or number of tests can be carried out essentially simultaneously, or analyses can be carried out over time. Moreover, fluid can be drawn continuously from the subject and one or more tests can be carried out of any number of points in time. A variety of reasons for carrying out one or more tests over the course of time exists, as would be understood by those of ordinary skill in the art. One such reason is to determine whether the quantity or another characteristic of an analyte is constant in a subject, or changes over time. A variety of specific techniques for continuous and/or discrete testing will be described herein.

Where microneedles are used, it can be advantageous to select needles of length such that interstitial fluid is preferentially obtained and, where not desirable, blood is not accessed. Those of ordinary skill in the art can arrange microneedles relative to the skin for these purposes including, in one embodiment, introducing microneedles into the skin at an angle, relative to the skin's surface, other than 90°, i.e., to introduce a needle or needles into the skin in a slanting fashion so as to access interstitial fluid.

In another aspect, the present invention is directed to a kit including one or more of the compositions previously discussed, e.g., a kit including a device for the delivery and/or receiving of fluid from the skin, a kit including a device able to determine a fluid, a kit including a drug and a device able to determine the drug within the skin, or the like. A "kit," as used herein, typically defines a package or an assembly including one or more of the compositions of the invention, and/or other compositions associated with the invention, for example, as previously described. Each of the compositions of the kit may be provided in liquid form (e.g., in solution), or in solid form (e.g., a dried powder). In certain cases, some of the compositions may be constitutable or otherwise processable (e.g., to an active form), for example, by the addition of a suitable solvent or other species, which may or may not be provided with the kit. Examples of other compositions or components associated with the invention include, but are not limited to, solvents, surfactants, diluents, salts, buffers, emulsifiers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, tapes, adhesives, and the like, for example, for using, administering, modifying, assembling, storing, packaging, preparing, mixing, diluting, and/or preserving the compositions components for a particular use, for example, to a sample and/or a subject.

A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, administering, assembly, storage, packaging, and/or preparation of the compositions and/or other compositions associated with the kit. In some cases, the instructions may also include instructions for the delivery and/or administration of the compositions, for example, for a particular use, e.g., to a sample and/or a subject. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

In some embodiments, the present invention is directed to methods of promoting one or more embodiments of the invention as discussed herein. As used herein, "promoted" includes all methods of doing business including, but not limited to, methods of selling, advertising, assigning, licensing, contracting, instructing, educating, researching, importing, exporting, negotiating, financing, loaning, trading, vending, reselling, distributing, repairing, replacing, insuring, suing, patenting, or the like that are associated with the systems, devices, apparatuses, articles, methods, compositions, kits, etc. of the invention as discussed herein. Methods of promotion can be performed by any party including, but not limited to, personal parties, businesses (public or private), partnerships, corporations, trusts, contractual or sub-contractual agencies, educational institutions such as colleges and universities, research institutions, hospitals or other clinical institutions, governmental agencies, etc. Promotional activities may include communications of any form (e.g., written, oral, and/or electronic communications, such as, but not limited to, e-mail, telephonic, Internet, Web-based, etc.) that are clearly associated with the invention.

In some embodiments, the method of promotion may involve one or more instructions. As used herein, "instructions" can define a component of instructional utility (e.g., directions, guides, warnings, labels, notes, FAQs or "frequently asked questions," etc.), and typically involve written instructions on or associated with the invention and/or with the packaging of the invention. Instructions can also include instructional communications in any form (e.g., oral, electronic, audible, digital, optical, visual, etc.), provided in any manner such that a user will clearly recognize that the instructions are to be associated with the invention, e.g., as discussed herein.

The following documents are incorporated herein by reference: U.S. Provisional Patent Application Ser. No. 61/058,796, filed Jun. 4, 2008, entitled "Compositions and Methods for Diagnostics, Therapies, and Other Applications"; U.S. Provisional Patent Application Ser. No. 61/163,791, filed Mar. 26, 2009, entitled "Composition and Methods for Rapid One-Step Diagnosis"; U.S. Provisional Patent Application Ser. No. 61/163,793, filed Mar. 26, 2009, entitled "Compositions and Methods for Diagnostics, Therapies, and Other Applications"; U.S. patent application Ser. No. 12/478,756, filed Jun. 4, 2009, entitled "Compositions and Methods for Diagnostics, Therapies, and Other Applications"; International Patent Application No. PCT/US09/046333, filed Jun. 4, 2009, entitled "Compositions and Methods for Diagnostics, Therapies, and Other Applications"; U.S. Provisional Patent Application Ser. No. 61/163,710, filed Mar. 26, 2009, entitled "Systems and Methods for Creating and Using Suction Blisters or Other Pooled Regions of Fluid within the Skin"; U.S. Provisional Patent Application Ser. No. 61/163,733, filed Mar. 26, 2009, entitled "Determination of Tracers within Subjects"; U.S. Provisional Patent Application Ser. No. 61/163,750, filed Mar. 26, 2009, entitled "Monitoring of Implants and Other Devices"; U.S. Provisional Patent Application Ser. No. 61/154,632, filed Mar. 2, 2009, entitled "Oxygen Sensor"; and U.S. Provisional Patent Application Ser. No. 61/269,436, filed Jun. 24, 2009, entitled "Devices and Techniques associated with Diagnostics, Therapies, and Other Applications, Including Skin-Associated Applications." Also incorporated herein by reference in its entirety is U.S. Provisional Patent Application Ser. No. 61/373,757, filed Aug. 13, 2010, entitled "Systems and Techniques for Monitoring Subjects," by Levinson, et al.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A device for application to a skin of a subject for treating the subject with a drug, the device comprising:
    a substance transfer component comprising one or more microneedles;
    a deployment actuator configured and arranged to move from a first position to a second position and from the second position to the first position, wherein when the deployment actuator is in the first position, the one or more microneedles do not contact the skin of the subject, and wherein when the deployment actuator is in the second position, at least one of the microneedles pierce the skin of the subject;
    a self-contained vacuum chamber having an internal pressure less than atmospheric pressure before the device is applied to the skin of the subject;
    a sensing chamber, positioned within the device, for containing the blood withdrawn from the subject, wherein the sensing chamber is separate from the self-contained vacuum chamber, and wherein the self-contained vacuum chamber is positioned within the device to withdraw a quantity of blood from the subject to be contained by the sensing chamber after the microneedles pierces the skin of the subject;
    a sensor positioned in sensing communication with the sensing chamber, the sensor being configured and arranged to determine an analyte suspected of being present within the blood within the sensing chamber;
    a microprocessor positioned in electrical communication with the sensor; and
    a drug reservoir within the device for containing the drug deliverable to the subject, wherein the device is configured to deliver the drug from the reservoir to the skin of the subject after the deployment actuator has moved from the first position to the second position and from the second position to the first position.

2. The device of claim 1, wherein the drug is deliverable to the subject from the drug reservoir via the substance transfer component.

3. The device of claim 1, wherein the device comprises a second substance transfer component for delivering the drug from the drug reservoir.

4. The device of claim 3, wherein the second substance transfer component comprises a needle.

5. The device of claim 1, the device further comprising a reaction entity contained within the sensing chamber able to react with the analyte suspected of being present within the blood.

6. The device of claim 1, the device further comprising a second actuator that, when actuated, fluidly communicates the pressure less than atmospheric pressure in the vacuum chamber to a site of piercing of the microneedles with the skin of the subject, wherein prior to actuating the second actuator, the pressure less than atmospheric pressure in the vacuum chamber is not in fluid communication with the site of piercing.

\* \* \* \* \*